United States Patent
Yoon et al.

(10) Patent No.: US 10,532,896 B2
(45) Date of Patent: Jan. 14, 2020

(54) GRIP APPARATUS AND SUBSTRATE INSPECTION SYSTEM INCLUDING THE SAME, AND METHOD OF MANUFACTURING SEMICONDUCTOR DEVICE USING THE SUBSTRATE INSPECTION SYSTEM

(71) Applicant: SAMSUNG ELECTRONICS CO., LTD., Suwon-si, Gyeonggi-Do (KR)

(72) Inventors: Kuihyun Yoon, Yongin-si (KR); Wonguk Seo, Gunpo-si (KR); Young Heo, Osan-si (KR)

(73) Assignee: SAMSUNG ELECTRONICS CO., LTD., Suwon-si, Gyeonggi-Do (KR)

( * ) Notice: Subject to any disclaimer, the term of this patent is extended or adjusted under 35 U.S.C. 154(b) by 0 days.

(21) Appl. No.: 15/991,668

(22) Filed: May 29, 2018

(65) Prior Publication Data

US 2019/0092580 A1 Mar. 28, 2019

(30) Foreign Application Priority Data

Sep. 26, 2017 (KR) .................. 10-2017-0124464

(51) Int. Cl.
*B65G 49/06* (2006.01)
*G01N 21/88* (2006.01)
*H01L 21/677* (2006.01)

(52) U.S. Cl.
CPC ....... *B65G 49/065* (2013.01); *G01N 21/8806* (2013.01); *H01L 21/67784* (2013.01)

(58) Field of Classification Search
CPC ................ B65G 49/065; B65G 49/064; G01N 21/8806; H01L 21/67784; H01L 21/67017; H01L 21/67242; H01L 21/67288; H01L 21/683; H01L 21/687
USPC ...................... 356/237.1–237.6, 239.1–239.8
See application file for complete search history.

(56) References Cited

U.S. PATENT DOCUMENTS

| | | | |
|---|---|---|---|
| 7,004,711 | B2 | 2/2006 | Ikehata et al. |
| 2007/0151296 | A1 | 7/2007 | Huh et al. |
| 2008/0069677 | A1 | 3/2008 | Kawachi et al. |

FOREIGN PATENT DOCUMENTS

| | | |
|---|---|---|
| JP | 2009229421 | 10/2009 |
| JP | 4435730 | 3/2010 |
| JP | 2010091435 | 4/2010 |
| KR | 100762393 | 10/2007 |
| KR | 100789659 | 12/2007 |
| KR | 101032089 | 5/2011 |
| KR | 101115874 | 2/2012 |

(Continued)

*Primary Examiner* — Tri T Ton
(74) *Attorney, Agent, or Firm* — F. Chan & Associates, LLC

(57) ABSTRACT

A substrate inspection system includes a floating unit that floats a substrate, an inspection unit disposed above the floating unit, a grip unit disposed below the inspection unit and including a first grip member that holds the substrate on the floating unit, a grip transfer unit that moves the grip unit in a first direction, and an illumination unit that generates light. The inspection unit inspects the substrate that floats on the floating unit, the illumination unit is disposed on a moving path of the grip unit, and the light generated by the illumination unit is irradiated onto the inspection unit. The first grip member includes a first adsorption pad that adsorbs the substrate, and a first support member that supports the first adsorption pad and that includes a first opening into which the illumination unit is inserted.

20 Claims, 19 Drawing Sheets

(56) References Cited

FOREIGN PATENT DOCUMENTS

| KR | 101270077 | 5/2013 |
| KR | 101384092 | 4/2014 |
| KR | 20160052192 | 5/2016 |
| KR | 20160078211 | 7/2016 |

GRIP APPARATUS AND SUBSTRATE INSPECTION SYSTEM INCLUDING THE SAME, AND METHOD OF MANUFACTURING SEMICONDUCTOR DEVICE USING THE SUBSTRATE INSPECTION SYSTEM

CROSS-REFERENCE TO RELATED APPLICATIONS

This U.S. nonprovisional patent application claims priority under 35 U.S.C. § 119 to Korean Patent Application No. 10-2017-0124464 filed on Sep. 26, 2017, the disclosure of which is hereby incorporated by reference in its entirety.

TECHNICAL FIELD

Exemplary embodiments of the inventive concept relate to a grip apparatus and a substrate inspection system including the same, and a method of manufacturing a semiconductor device using the substrate inspection system.

DISCUSSION OF THE RELATED ART

As semiconductor processes become more complex, the importance of inspecting particles produced on semiconductor devices is increasing. The inspection of particles on semiconductor substrates, and the reduction of particles, may improve the reliability of semiconductor devices and may increase process yield. An optical apparatus may be used to inspect particles on semiconductor substrates.

SUMMARY

Exemplary embodiments of the inventive concept provide a grip apparatus for reducing or minimizing a non-inspected area(s) of a substrate, and a substrate inspection system including the same.

According to an exemplary embodiment of the inventive concept, a substrate inspection system includes a floating unit that floats a substrate, an inspection unit disposed above the floating unit, a grip unit disposed below the inspection unit and including a first grip member that holds the substrate on the floating unit, a grip transfer unit that moves the grip unit in a first direction, and an illumination unit that generates light. The inspection unit inspects the substrate that floats on the floating unit, the illumination unit is disposed on a moving path of the grip unit, and the light generated by the illumination unit is irradiated onto the inspection unit. The first grip member includes a first adsorption pad that adsorbs the substrate, and a first support member that supports the first adsorption pad and that includes a first opening into which the illumination unit is inserted.

According to an exemplary embodiment of the inventive concept, a substrate inspection system includes a floating unit that floats a substrate, a grip unit that holds the substrate on the floating unit, a first illumination member disposed between the first and second grip members, and a grip transfer unit that moves the grip unit. The grip unit includes a first grip member and a second grip member spaced apart from each other, and the first illumination member irradiates a light onto the substrate. Each of the first and second grip members includes an adsorption pad that adsorbs the substrate, a support stand disposed below the adsorption pad and spaced apart from the adsorption pad in a direction away from the first illumination member, and a support plate connecting the adsorption pad to the support stand.

According to an exemplary embodiment of the inventive concept, a grip apparatus includes a tray, a first grip member disposed on the tray, and a second grip member disposed on the tray and spaced apart from the first grip member in a first direction. The first grip member includes a first support member including a first support plate spaced apart from the tray, a first support stand connecting the first support plate to the tray, a first opening, and a first adsorption pad. The first opening extends in a first direction between a first lateral surface of the first support plate and an inner surface of the first support stand. The first lateral surface faces the second grip member. The first adsorption pad is disposed on the first support plate and adsorbs a substrate, and is adjacent to the first lateral surface.

According to an exemplary embodiment of the inventive concept, a method of manufacturing a semiconductor device includes forming the semiconductor device using a substrate, and testing the substrate using a substrate inspection system. Testing the substrate using the substrate inspection system includes floating the substrate using a floating unit of the substrate inspection system, and holding the substrate on the floating unit using a grip unit of the substrate inspection system. The grip unit includes a first grip member and a second grip member spaced apart from each other. Testing the substrate further includes moving the grip unit by a grip transfer unit of the substrate inspection system, and generating a light by an illumination member disposed between the first and second grip members. The light is irradiated onto the substrate. Testing the substrate further includes inspecting the substrate floating on the floating unit by an inspection unit of the substrate inspection system. The light is irradiated onto the inspection unit through the substrate, and the inspection unit inspects the substrate using the light irradiated onto the inspection unit. Each of the first and second grip members includes an adsorption pad that adsorbs the substrate, a support stand disposed below the adsorption pad and spaced apart from the adsorption pad in a direction away from the illumination member, and a support plate connecting the adsorption pad to the support stand.

BRIEF DESCRIPTION OF THE DRAWINGS

The above and other features of the present inventive concept will become more apparent by describing in detail exemplary embodiments thereof with reference to the accompanying drawings, in which.

DETAILED DESCRIPTION OF THE EXEMPLARY EMBODIMENTS

Figure 1:
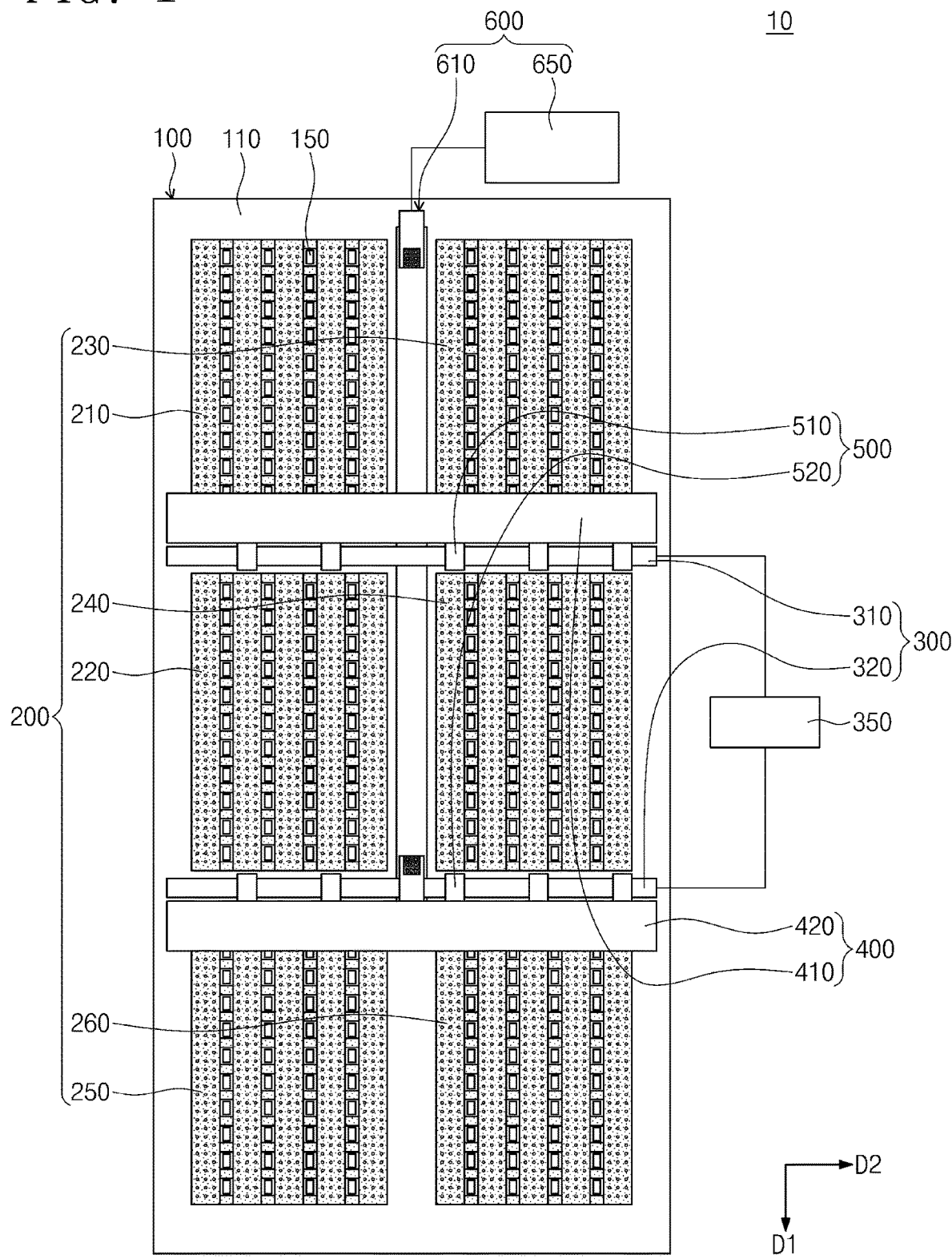
FIG. 1 illustrates a plan view showing a substrate inspection system according to an exemplary embodiment of the inventive concept.

Exemplary embodiments of the present inventive concept will be described more fully hereinafter with reference to the accompanying drawings. Like reference numerals may refer to like elements throughout the accompanying drawings.

Spatially relative terms, such as "beneath", "below", "lower", "under", "above", "upper", etc., may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" or "under" other elements or features would then be oriented "above" the other elements or features. Thus, the exemplary terms "below" and "under" can encompass both an orientation of above and below.

It will be understood that when a component, such as a film, a region, a layer, or an element, is referred to as being "on", "connected to", "coupled to", or "adjacent to" another component, it can be directly on, connected, coupled, or adjacent to the other component, or intervening components may be present. It will also be understood that when a component is referred to as being "between" two components, it can be the only component between the two components, or one or more intervening components may also be present. It will also be understood that when a component is referred to as "covering" another component, it can be the only component covering the other component, or one or more intervening components may also be covering the other component.

It will be understood that the terms "first," "second," "third," etc. are used herein to distinguish one element from another, and the elements are not limited by these terms. Thus, a "first" element in an exemplary embodiment may be described as a "second" element in another exemplary embodiment.

Herein, when two or more elements or values are described as being substantially the same as or about equal to each other, it is to be understood that the elements or values are identical to each other, indistinguishable from each other, or distinguishable from each other but functionally the same as each other as would be understood by a person having ordinary skill in the art. It will be further understood that when two components or directions are described as extending substantially parallel or perpendicular to each other, the two components or directions extend exactly parallel or perpendicular to each other, or extend approximately parallel or perpendicular to each other as would be understood by a person having ordinary skill in the art.

Figure 2:
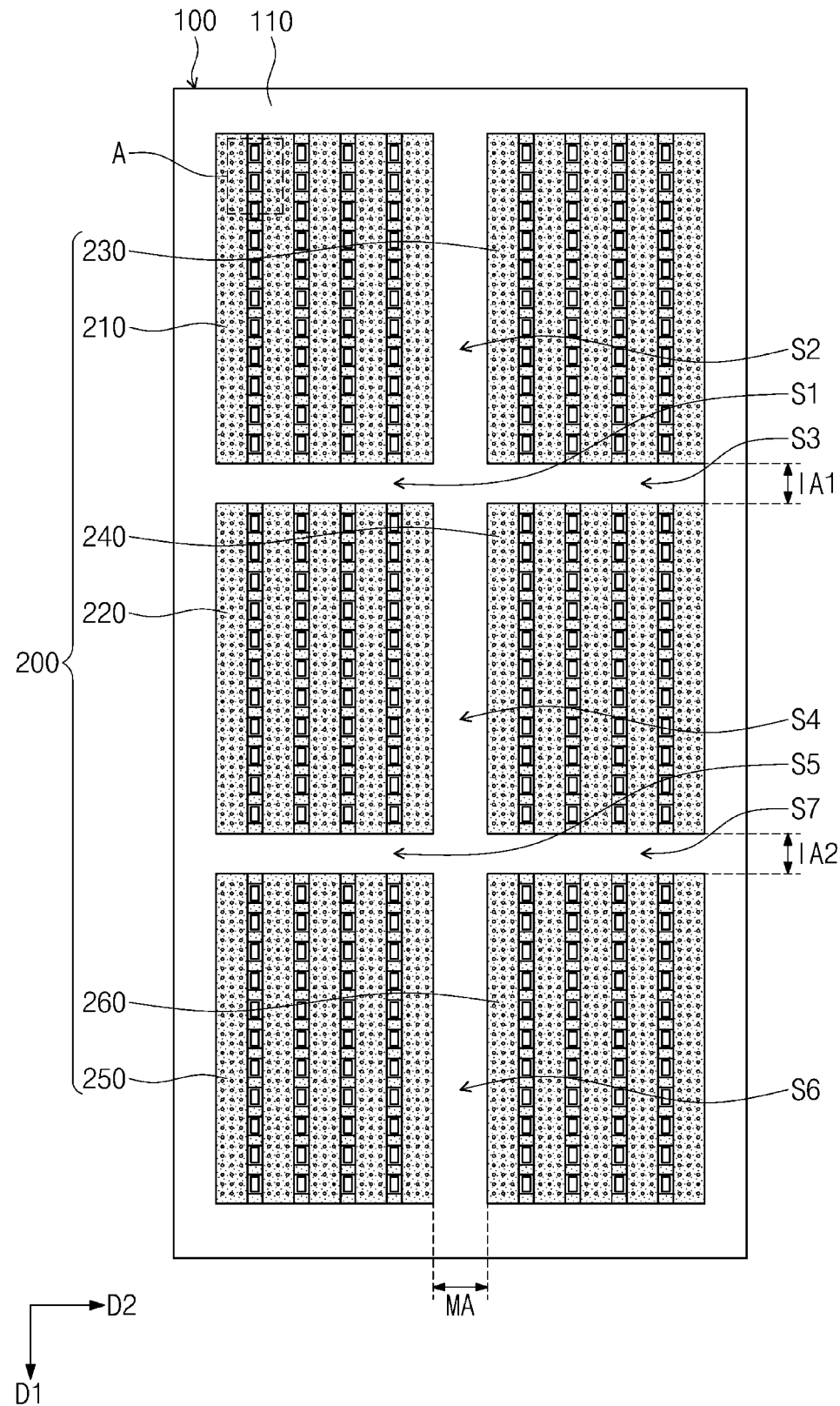
FIG. 2 illustrates a plan view partially showing the substrate inspection system of FIG. 1 according to an exemplary embodiment of the inventive concept.
Figure 3:
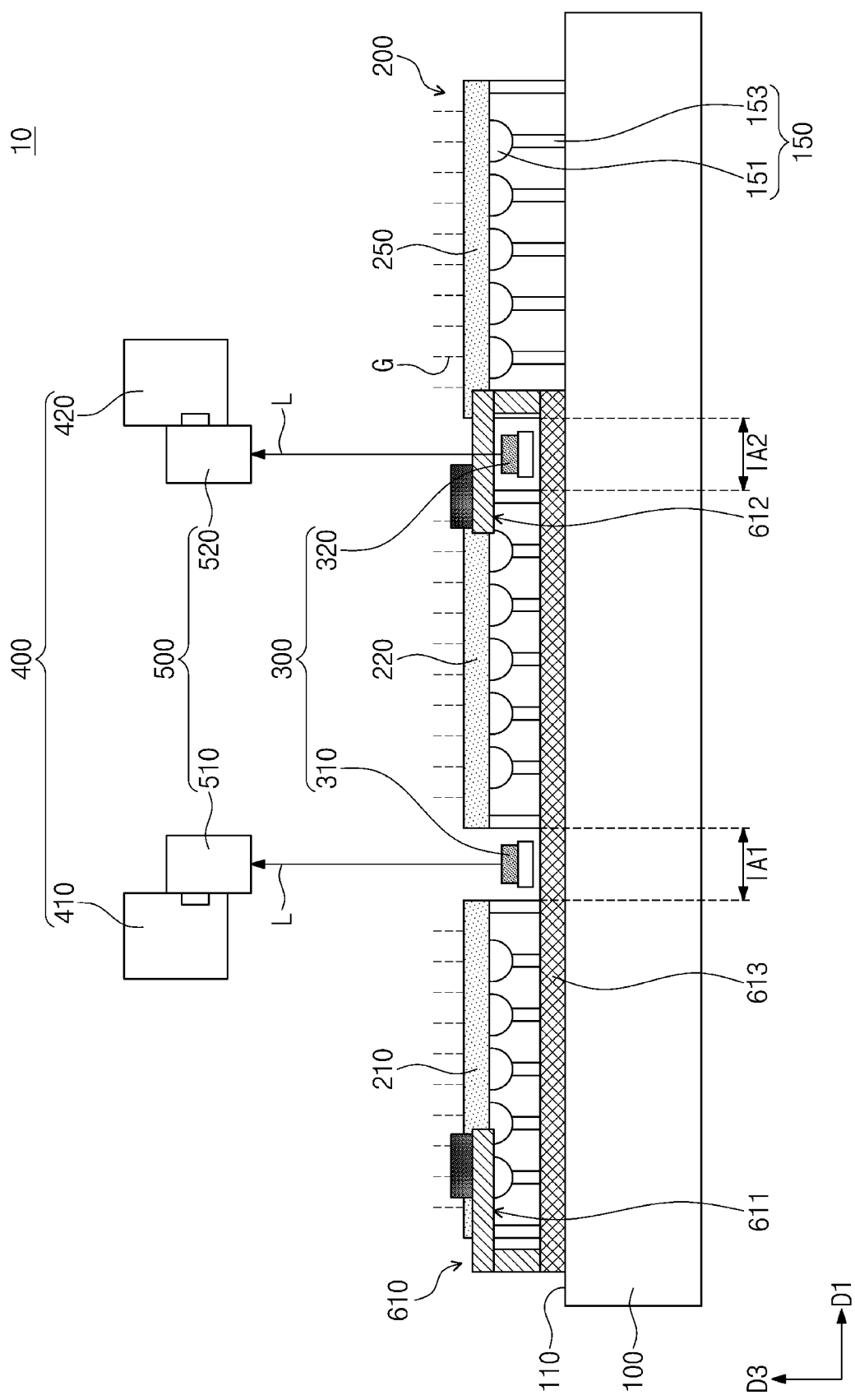
FIG. 3 illustrates a side view showing the substrate inspection system of FIG. 1 according to an exemplary embodiment of the inventive concept.
Figure 4:
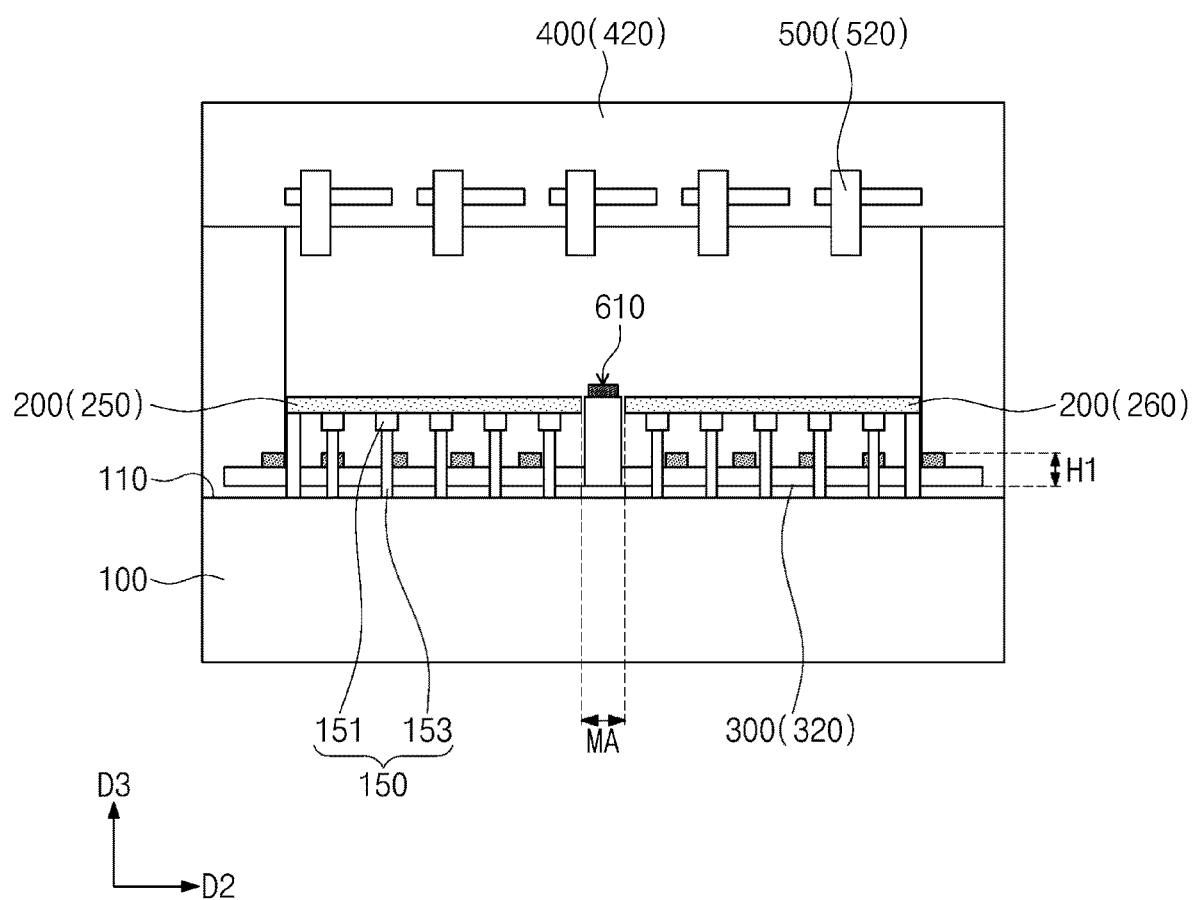
FIG. 4 illustrates a front view showing the substrate inspection system of FIG. 1 according to an exemplary embodiment of the inventive concept.
Figure 5:
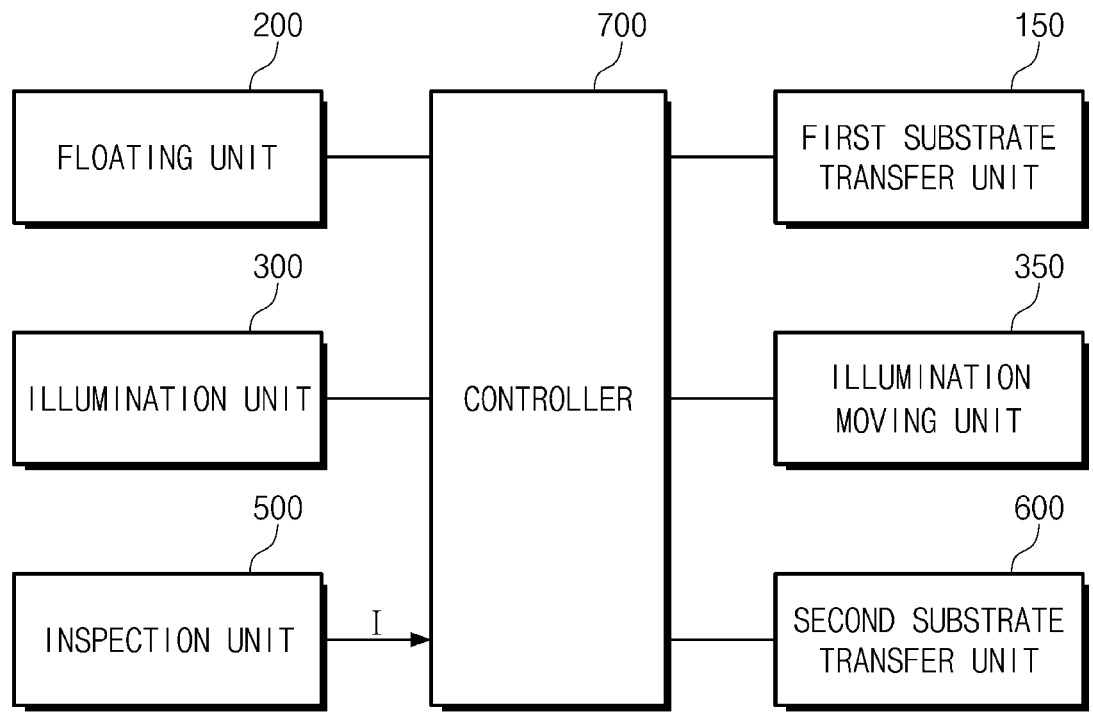
FIG. 5 illustrates a block diagram partially showing the substrate inspection system of FIG. 1 according to an exemplary embodiment of the inventive concept.
Figure 6:
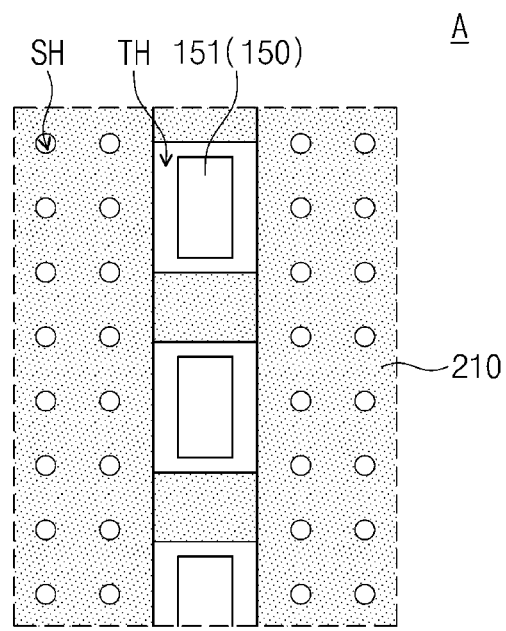
FIG. 6 illustrates an enlarged view showing section A of FIG. 2 according to an exemplary embodiment of the inventive concept.

FIG. 1 illustrates a plan view showing a substrate inspection system according to an exemplary embodiment of the inventive concept. FIG. 2 illustrates a plan view partially showing the substrate inspection system of FIG. 1 according to an exemplary embodiment of the inventive concept. FIG. 3 illustrates a side view showing the substrate inspection system of FIG. 1 according to an exemplary embodiment of the inventive concept. FIG. 4 illustrates a front view showing the substrate inspection system of FIG. 1 according to an exemplary embodiment of the inventive concept. FIG. 5 illustrates a block diagram partially showing the substrate inspection system of FIG. 1 according to an exemplary embodiment of the inventive concept. FIG. 6 illustrates an enlarged view showing section A of FIG. 2 according to an exemplary embodiment of the inventive concept.

Referring to FIGS. 1 to 6, a substrate inspection system 10 according to exemplary embodiments of the inventive concept uses light to inspect whether a defect(s) is present on a substrate that is used to manufacture a semiconductor device. The substrate allows light to pass therethrough. For example, the substrate may be or may include a glass panel that allows light to pass therethrough. However, exemplary embodiments of the inventive concept are not limited thereto. The substrate inspection system 10 may include a base 100, a gantry 400, a floating unit 200, a first substrate transfer unit 150, an illumination unit 300, an illumination moving unit 350, an inspection unit 500, a second substrate transfer unit 600, and a controller 700.

The base 100 supports components of the substrate inspection system 10. For example, the base 100 may support the gantry 400, the floating unit 200, a portion of the second substrate transfer unit 600, the illumination unit 300, and the first substrate transfer unit 150.

The floating unit 200 may cause the substrate to float above the floating unit 200. For example, the floating unit 200 may inject gas G (e.g., air) toward the substrate, thereby floating the substrate. In this description, the term "float" means that the substrate floats above the floating unit 200 while being spaced apart from the floating unit 200.

The floating unit 200 may be placed on a top surface 110 of the base 100. The floating unit 200 may include a plurality of floating stages 210, 220, 230, 240, 250, and 260 that are spaced apart from one another, and a gas supply that supplies the gas G to the floating stages 210 to 260.

The floating stages 210 to 260 may be, when viewed in a plan view, arranged along a first direction D1 and a second direction D2 substantially perpendicular to the first direction D1, as shown in FIG. 1. Each of the floating stages 210 to 260 may include a plurality of spray holes SH on its top surface, as shown in FIG. 6. The spray holes SH may be, when viewed in a plan view, arranged along the first and second directions D1 and D2, as shown in FIG. 6. Each of the floating stages 210 to 260 may be configured such that the gas G is injected upward through the spray holes SH. Accordingly, the substrate may float above the floating stages 210 to 260 as a result of the gas G being injected upward through the spray holes SH. Each of the floating stages 210 to 260 may include a plurality of through holes TH on its top surface, as shown in FIG. 6. The plurality of through holes TH may be arranged along the first and second directions D1 and D2, as shown in FIG. 6.

In an exemplary embodiment, the floating unit 200 may include first to sixth floating stages 210, 220, 230, 240, 250, and 260. Each of the first to sixth floating stages 210 to 260 may be provided in the form of a rectangle when viewed in a plan view. However, exemplary embodiments of the inventive concept are not limited thereto.

The second floating stage 220 may be spaced apart from the first floating stage 210 in the first direction D1, as shown in FIGS. 1 and 2. In such a configuration, a first space S1 may be disposed between the first and second floating stages 210 and 220, as shown in FIG. 2.

The third floating stage 230 may be spaced apart from the first floating stage 210 in the second direction D2, as shown in FIGS. 1 and 2. Accordingly, a second space S2 may be disposed between the first and third floating stages 210 and 230, as shown in FIG. 2.

The fourth floating stage 240 may be spaced apart from the second floating stage 220 in the second direction D2, as shown in FIGS. 1 and 2. The fourth floating stage 240 may be spaced apart from the third floating stage 230 in the first direction D1, as shown in FIGS. 1 and 2. Therefore, a third space S3 may be disposed between the third and fourth floating stages 230 and 240, and a fourth space S4 may be disposed between the second and fourth floating stages 220 and 240, as shown in FIG. 2.

The fifth floating stage 250 may be spaced apart from the second floating stage 220 in the first direction D1, as shown in FIGS. 1 and 2. Thus, a fifth space S5 may be disposed between the second and fifth floating stages 220 and 250.

The sixth floating stage 260 may be spaced apart from the fifth floating stage 250 in the second direction D2, as shown in FIGS. 1 and 2. The sixth floating stage 260 may be spaced apart from the fourth floating stage 240 in the first direction D1, as shown in FIGS. 1 and 2. Therefore, a sixth space S6 may be disposed between the fifth and sixth floating stages 250 and 260, and a seventh space S7 may be disposed between the fourth and sixth floating stages 240 and 260, as shown in FIG. 2.

The second, fourth, and sixth spaces S2, S4, and S6 may be, when viewed in a plan view, sequentially arranged along the first direction D1, as shown in FIG. 2. The second, fourth, and sixth spaces S2, S4, and S6 may lie on the same line. For example, the second, fourth, and sixth spaces S2, S4, and S6 may be aligned with one another in the first direction D1 to form a continuous space extending in the first direction D1 between the floating stages. Hereinafter, an area overlapping (e.g., vertically overlapping) the second, fourth, and sixth spaces S2, S4, and S6 is called a movement area MA of a grip unit 610. The movement area MA may be, when viewed in a plan view, formed along the first direction D1, as shown in FIG. 2. The movement area MA is formed by a combination of the second, fourth, and sixth spaces S2, S4, and S6. In an exemplary embodiment, the movement area MA may extend across the floating unit 200 along the first direction D1.

Each of the first, third, fifth, and seventh spaces S1, S3, S5, and S7 may extend, when viewed in a plan view, along the second direction D2, as shown in FIG. 2. The first and third spaces S1 and S3 may lie on the same line. For example, the first and third spaces S1 and S3 may be aligned with one another in the second direction D2 to form a continuous space extending in the second direction D2 between some of the floating stages, as shown in FIG. 2. Hereinafter, an area overlapping (e.g., vertically overlapping) the first and third spaces S1 and S3 is called a first inspection area IA1.

The fifth and seventh spaces S5 and S7 may lie on the same line. For example, the fifth and seventh spaces S5 and S7 may be aligned with one another in the second direction D2 to form a continuous space extending in the second direction D2 between some of the floating stages, as shown in FIG. 2. An area overlapping (e.g., vertically overlapping) the fifth and seventh spaces S5 and S7 is called a second inspection area IA2. The first and second inspection areas IA1 and IA2 may extend across the floating unit 200 in the second direction D2, as shown in FIG. 2. In an exemplary embodiment, the first and second inspection areas IA1 and IA2 may substantially intersect (e.g., substantially vertically intersect) the movement area MA. For example, as shown in FIG. 2, the first and second inspection areas IA1 and IA2 extend in the second direction D2, and the movement area MA extends in the first direction D1. In an exemplary embodiment, the first and second directions D1 and D2 are substantially perpendicular to each other. Thus, in an exemplary embodiment, the first and second inspection areas IA1 and IA2 extend substantially perpendicular to the movement area MA and intersect the movement area MA.

The first substrate transfer unit 150 may transfer the substrate to the floating unit 200. In an exemplary embodiment, the first substrate transfer unit 150 may transfer the substrate that does not float by the floating unit 200. The first substrate transfer unit 150 may transfer the substrate in the first direction D1. The first substrate transfer unit 150 may be placed on the top surface 110 of the base 100. The first substrate transfer unit 150 may include a plurality of rollers 151, a rotating part, and an elevating part 153.

The rollers 151 may be, when viewed in a plan view, arranged along the first and second directions D1 and D2. The rollers 151 may overlap (e.g., vertically overlap) the through holes TH, as shown in FIG. 3. The elevating part 153 may raise or lower the rollers 151. The elevating part 153 may thus pass the rollers 151 through the through holes TH. The elevating part 153 may be or may include a hydraulic or pneumatic cylinder. However, exemplary embodiments of the inventive concept are not limited thereto. The rotating part may rotate the rollers 151. The rotating part may be or may include a rotary motor. However, exemplary embodiments of the inventive concept are not limited thereto.

The gantry 400 may be disposed on the top surface 110 of the base 100, as shown in FIG. 3. In an exemplary embodiment, the gantry 400 may include a first gantry 410 and a second gantry 420 spaced apart from the first gantry 410 in the first direction D1. The first and second gantries 410 and 420 may be rigidly connected to the base 100. The first and second gantries 410 and 420 may have the same structure as each other. The gantry 400 will be described below in further detail with reference to FIG. 9.

The inspection unit 500 may be disposed above the floating unit 200, the illumination unit 300, and the grip unit 610, as shown in FIG. 3. For example, the inspection unit 500 may be spaced apart from the floating unit 200, the illumination unit 300, and the grip unit 610 in a third direction D3 that is substantially perpendicular to the first and second directions D1 and D2. The inspection unit 500 may be engaged with the gantry 400 (e.g., the inspection unit 500 and the gantry 400 may be physically coupled to each other). The inspection unit 500 may inspect the substrate that floats by the floating unit 200. The inspection unit 500 may include a plurality of optical members 510 and 520, and an optical-member moving part that moves the optical members 510 and 520.

The plurality of optical members 510 and 520 may include first optical members 510 that are movably engaged with the first gantry 410, and second optical members 520 that are movably engaged with the second gantry 420. In an exemplary embodiment, the first and second optical members 510 and 520 may include charge-coupled device cameras. However, exemplary embodiments of the inventive concept are not limited thereto. The first and second optical members 510 and 520 may use light generated by first and second illumination members 310 and 320 which will be discussed below, thereby photographing the substrate. Accordingly, the first and second optical members 510 and 520 may obtain image information I of the substrate. The obtained image information I may be transmitted to the controller 700.

The first optical members 510 may be arranged at a regular distance along the second direction D2. For example, in an exemplary embodiment, the distance between adjacent first optical members 510 arranged in the second direction D2 is about equal for all of the first optical members 510. The first optical members 510 may overlap (e.g., vertically overlap) the first and third spaces S1 and S3. For example, the first optical members 510 may be positioned within the first inspection area IA1 (see FIG. 2).

The second optical members 520 may be arranged at a regular distance along the second direction D2. For example, in an exemplary embodiment, the distance between adjacent second optical members 520 arranged in the second direction D2 is about equal for all of the second optical members 520. The second optical members 520 may overlap (e.g., vertically overlap) the fifth and seventh spaces S5 and S7. For example, the second optical members 520 may be positioned within the second inspection area IA2 (see FIG. 2).

The optical-member moving part may drive each of the optical members 510 and 520 to reciprocally move in the second direction D2 and a reverse direction opposite to the second direction D2. Accordingly, each of the optical members 510 and 520 may inspect a portion of the substrate, while reciprocally moving a certain distance. In an exemplary embodiment, the optical-member moving part may be or may include a linear motor. However, exemplary embodiments of the inventive concept are not limited thereto.

The illumination unit 300 may generate light L in a direction toward the inspection unit 500, thereby irradiating the inspection unit 500 with the light L. For example, the light L generated by the illumination unit 300 may be irradiated onto the substrate, and pass through the substrate to also be irradiated onto the inspection unit 500. In an exemplary embodiment, the illumination unit 300 is disposed beneath the inspection unit 500 and the floating unit 200, and the substrate is positioned between the illumination unit 300 and the inspection unit 500. In such a configuration, the illumination unit 300 may generate the light L in a direction toward the substrate on the floating unit 200, thereby irradiating the substrate with the light L (see FIG. 18). The illumination unit 300 may be disposed on a moving path of the grip unit 610, while running across the moving path of the grip unit 610, which will be discussed further below. The illumination unit 300 may include one or more illumination members 310 and 320. For example, the grip unit 610 moves in the movement area MA (see FIG. 2), and a portion of the illumination unit 300 is disposed in the movement area MA in which the grip unit 610 moves. For example, as shown in FIGS. 1 and 2, the first illumination member 310 extends in the second direction D2 in an area corresponding to the first inspection area IA1 and crosses the movement area MA, resulting in a portion of the first illumination member 310 being disposed on a moving path of the grip unit 610. Similarly, the second illumination member 320 extends in the second direction D2 in an area corresponding to the second inspection area IA2 and crosses the movement area MA, resulting in a portion of the second illumination member 320 being disposed on a moving path of the grip unit 610.

In an exemplary embodiment, the illumination unit 300 may include a first illumination member 310 and a second illumination member 320 spaced apart from the first illumination member 310 in the first direction D1, as shown in FIG. 3. Each of the first and second illumination members 310 and 320 may have a bar shape elongated along the second direction D2. The first and second illumination members 310 and 320 may generate the light L in an upward direction.

The first illumination member 310 may be disposed between the first and second floating stages 210 and 220 and/or between the third and fourth floating stages 230 and 240. The first illumination member 310 may overlap (e.g., vertically overlap) the first and third spaces S1 and S3. For example, the first illumination member 310 may be positioned within the first inspection area IA1. The first illumination member 310 may overlap (e.g., vertically overlap) the first optical members 510.

The second illumination member 320 may be disposed between the second and fifth floating stages 220 and 250 and/or between the fourth and sixth floating stages 240 and 260. The second illumination member 320 may overlap (e.g., vertically overlap) the fifth and seventh spaces S5 and S7. The second illumination member 320 may be positioned within the second inspection area IA2. The second illumination member 320 may overlap (e.g., vertically overlap) the second optical members 520. Each of the first and second illumination members 310 and 320 may have a height H1 (see FIG. 4). In this description, the term "height" denotes a length in the third direction D3.

The illumination moving unit 350 may provide a driving force to the illumination unit 300. The illumination moving unit 350 may therefore move the illumination unit 300. In an exemplary embodiment, the illumination moving unit 350 may drive the first and second illumination members 310 and 320 to move them in the second direction D2 and in a reverse direction opposite to the second direction D2. The illumination moving unit 350 may be or may include a linear motor. However, exemplary embodiments of the inventive concept are not limited thereto.

The second substrate transfer unit 600 may drive the substrate to move on the floating unit 200. For example, the second substrate transfer unit 600 may transfer the substrate that floats by the floating unit 200. The second substrate transfer unit 600 may include the grip unit 610 and a grip transfer unit 650, as shown in FIG. 1.

The grip unit 610 may hold the substrate on the floating unit 200. The grip unit 610 may be disposed beneath the inspection unit 500. In an exemplary embodiment, the grip unit 610 may lie on the movement area MA. For example, the grip unit 610 may be disposed in and move within the movement area MA. The grip unit 610 may include a first grip member 611, a second grip member 612, and a tray 613, as shown in FIG. 3.

The first and second grip members 611 and 612 may hold the substrate. For example, the first and second grip members 611 and 612 may grip an edge of the substrate. The second grip member 612 may be spaced apart from the first grip member 611 in the first direction D1. The first and second grip members 611 and 612 may be spaced apart from each other across the illumination unit 300. For example, the illumination unit 300 may lie between the first and second grip members 611 and 612, as shown in FIG. 3. The grip unit 610 will be discussed below in further detail.

The grip transfer unit 650 may move the grip unit 610. For example, the grip transfer unit 650 may drive the grip unit 610 to move the grip unit 610 in the first direction D1 and in a reverse direction opposite to the first direction D1. In an exemplary embodiment, the grip transfer unit 650 may drive the grip unit 610 to reciprocally move within the movement area MA. Accordingly, the grip transfer unit 650 may drive the grip unit 610 to move between the first and third floating stages 210 and 230, between the second and fourth floating stages 220 and 240, and between the fifth and sixth floating stages 250 and 260. In this sense, the floating unit 200 may not interfere when the grip transfer unit 650 moves the grip unit 610.

The grip transfer unit 650 may move the tray 613 to thereby transfer the grip unit 610. Therefore, the grip transfer unit 650 may simultaneously move the first and second grip members 611 and 612 that are positioned on the tray 613. The grip transfer unit 650 may include various driving means capable of moving the grip unit 610. For example, the grip transfer unit 650 may include a linear motor. However, the grip transfer unit 650 is not limited thereto.

The controller 700 may control operations of the first substrate transfer unit 150, the floating unit 200, the grip unit 610, the grip transfer unit 650, the illumination unit 300, and the inspection unit 500. The controller 700 may use the image information I obtained by the inspection unit 500 to detect defects of the substrate.

Figure 7:
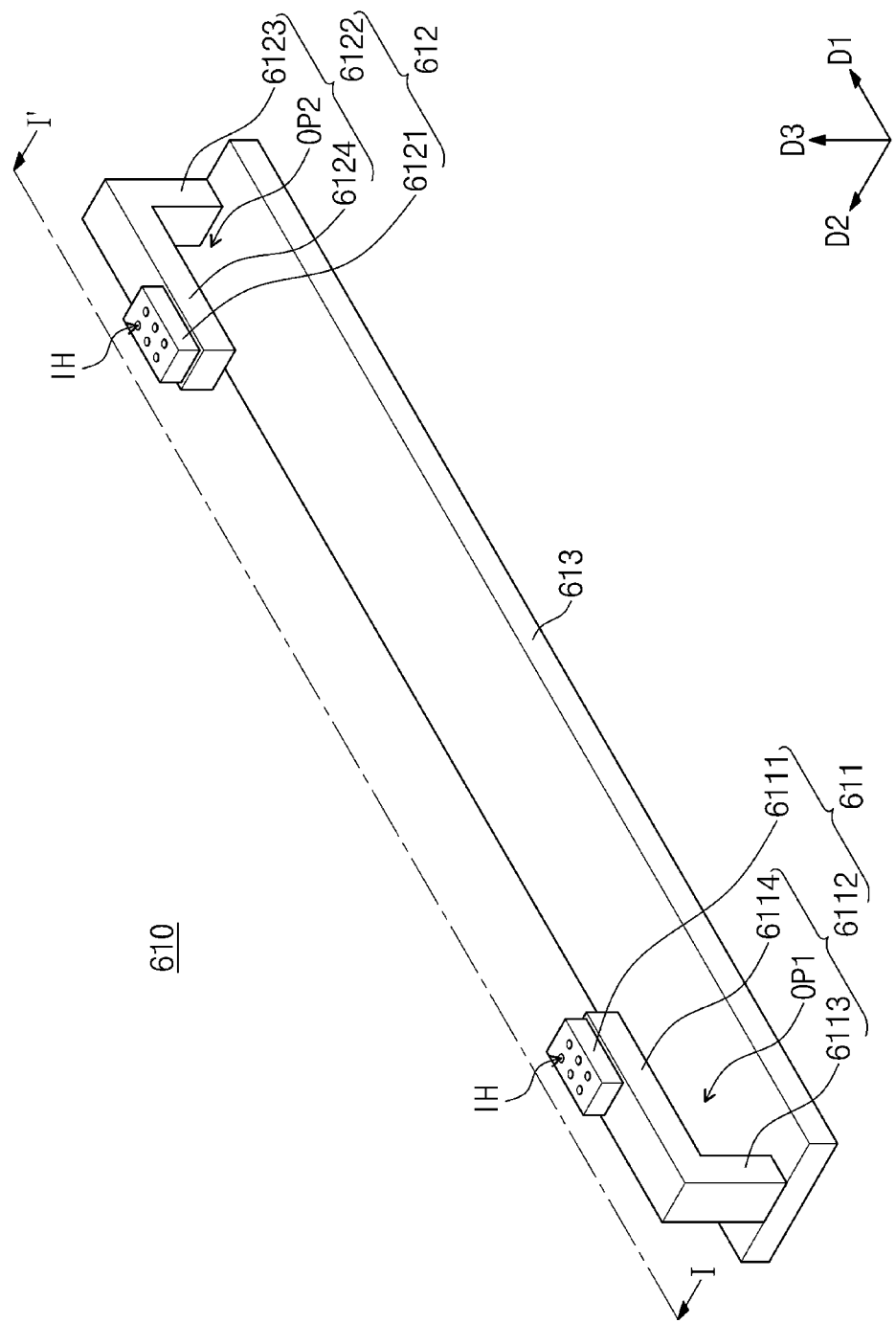
FIG. 7 illustrates a perspective view showing the grip unit of FIG. 1 according to an exemplary embodiment of the inventive concept.
Figure 8:
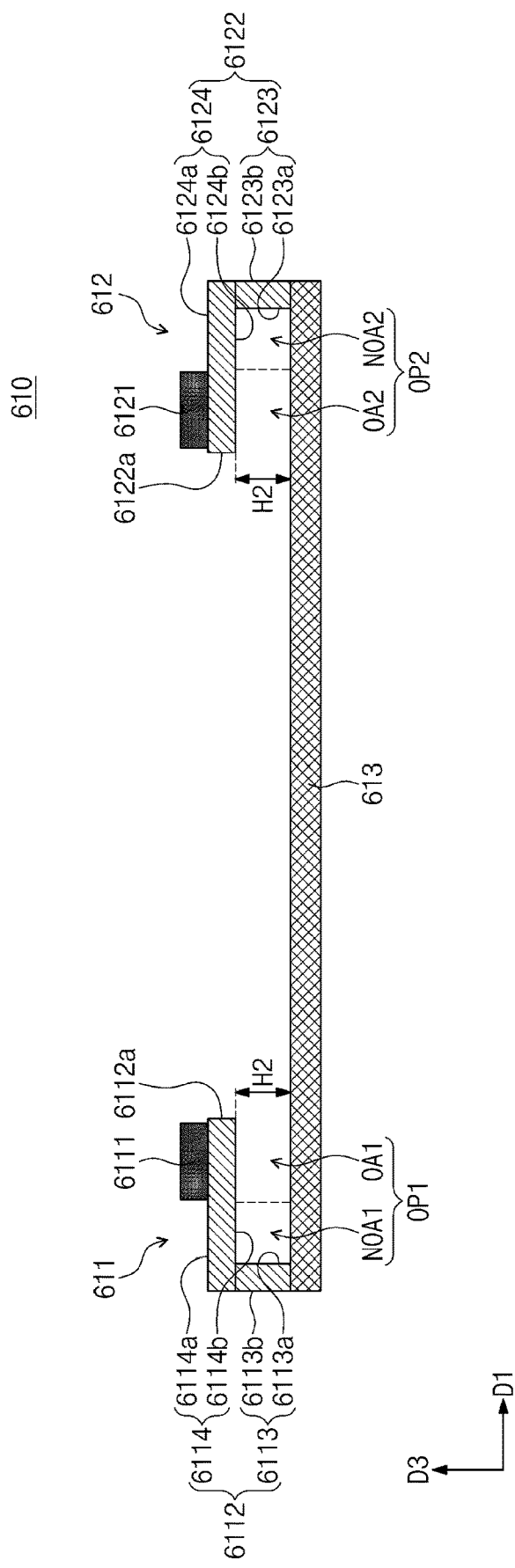
FIG. 8 illustrates a cross-sectional view taken along line I-I' of FIG. 7 according to an exemplary embodiment of the inventive concept.

FIG. 7 illustrates a perspective view showing a grip unit of FIG. 1 according to an exemplary embodiment of the inventive concept. FIG. 8 illustrates a cross-sectional view taken along line I-I' of FIG. 7 according to an exemplary embodiment of the inventive concept.

Referring to FIGS. 3, 6, 7, and 8, the grip unit 610 may include the first grip member 611, the second grip member 612, and the tray 613.

The tray 613 may support the first and second grip members 611 and 612. The tray 613 may connect the first and second grip members 611 and 612 that are spaced apart from each other. The tray 613 may be elongated in the first direction D1. The tray 613 may be placed beneath the floating unit (see 200 of FIG. 3) and the illumination unit (see 300 of FIG. 3). In an exemplary embodiment, the tray 613 may move along a rail provided on the base 100.

The first grip member 611 may be placed on the tray 613. In an exemplary embodiment, the first grip member 611 may be adjacent to an end of the tray 613. The first grip member 611 may include a first adsorption pad 6111 and a first support member 6112.

The first support member 6112 may support the first adsorption pad 6111. The first support member 6112 may have a first opening OP1 into which the illumination unit 300 is inserted. In an exemplary embodiment, the first illumination member (see 310 of FIG. 3) may be inserted into the first opening OP1.

As shown in FIGS. 7 and 8, the first support member 6112 may include a first lateral surface 6112a facing the second grip member 612 and a third lateral surface opposite to the first lateral surface 6112a. The first opening OP1 may be recessed toward the third lateral surface from the first lateral surface 6112a. For example, the first opening OP1 may extend in the first direction D1 between the first lateral surface 6112a and an inner surface 6113a of the first support stand 6113. The first support member 6112 may include a first support plate 6114 and a first support stand 6113. In an exemplary embodiment, the first support plate 6114 and the first support stand 6113 may be integrally formed as a single body.

The first support plate 6114 may be spaced apart from the tray 613 in the third direction D3. The first support plate 6114 may have a top surface 6114a and a bottom surface 6114b facing each other. In this description, the term "facing" means positioned on opposing sides. The bottom surface 6114b of the first support plate 6114 may face the tray 613. The first support plate 6114 may connect the first adsorption pad 6111 and the first support stand 6113 that are spaced apart from each other. The first support plate 6114 may have a rectangular shape when viewed in plan view. However, exemplary embodiments of the inventive concept are not limited thereto.

The first support stand 6113 may be located between and connect the first support plate 6114 and the tray 613. The first support stand 6113 may be disposed beneath the bottom surface 6114b of the first support plate 6114. The first support stand 6113 may be disposed on a top surface of the tray 613. The first support stand 6113 may be disposed below the first adsorption pad 6111.

The first support stand 6113 and the first adsorption pad 6111 may be spaced apart from each other in the first direction D1, as shown in FIGS. 7 and 8. The first support stand 6113 may be adjacent to a first end of the first support plate 6114. The first support stand 6113 may include an inner surface 6113a facing the second grip member 612 and an outer surface 6113b opposite to the inner surface 6113a. The first support stand 6113 may be disposed substantially perpendicular to the first support plate 6114.

The first lateral surface 6112a may include a second end of the first support plate 6114. The third lateral surface may include the first end of the first support plate 6114 and the outer surface 6113b of the first support stand 6113.

The first adsorption pad 6111 may adsorb the substrate. For example, the first adsorption pad 6111 may be supplied with negative pressure from an adsorption unit (e.g., a vacuum pump), thereby holding the substrate. Thus, the first grip member 611 may grip the substrate. The first adsorption pad 6111 may include on its top surface a plurality of inhale holes IH.

The first adsorption pad 6111 may be disposed on the first support member 6112. For example, the first adsorption pad 6111 may lie on the top surface 6114a of the first support plate 6114, as shown in FIG. 8. The first adsorption pad 6111 may be adjacent to the second end of the first support plate 6114. The first adsorption pad 6111 may be spaced apart from the first support stand 6113 in the first direction D1. The first adsorption pad 6111 may include a resilient material. For example, the first adsorption pad 6111 may include an acrylonitrile-butadiene rubber.

The first opening OP1 may be defined by the first support plate 6114 and the first support stand 6113. The first opening OP1 may be disposed beneath the bottom surface 6114*b* of the first support plate 6114. In an exemplary embodiment, the first opening OP1 may be disposed between the first support plate 6114 and the tray 613. For example, the first opening OP1 may be located between the first adsorption pad 6111 and the tray 613. The first opening OP1 may have a height H2 greater than the height H1 of the first illumination member 310. The height H2 of the first opening OP1 may indicate a spacing distance between the tray 613 and the bottom surface 6114*b* of the first support plate 6114. The first opening OP1 may include a first overlapping area OA1 and a first non-overlapping area NOA1.

The first opening OP1 may have a portion that overlaps the first adsorption pad 6111 and corresponds to the first overlapping area OA1. The first opening OP1 may also have another portion that does not overlap the first adsorption pad 6111 and that corresponds to the first non-overlapping area NOA1. The first non-overlapping area NOA1 may be positioned between the first overlapping area OA1 and the inner surface 6113*a* of the first support stand 6113.

The second grip member 612 may be disposed on the tray 613. In an exemplary embodiment, the second grip member 612 may be adjacent to an opposite end of the tray 613. The second grip member 612 may include a second adsorption pad 6121 and a second support member 6122.

The second support member 6122 may support the second adsorption pad 6121. The second support member 6122 may have a second opening OP2 into which the illumination unit 300 is inserted. In an exemplary embodiment, the second illumination member (see 320 of FIG. 3) may be inserted into the second opening OP2.

The second support member 6122 may include a second lateral surface 6122*a* facing the first grip member 611 and a fourth lateral surface opposite to the second lateral surface 6122*a*. The second opening OP2 may be recessed toward the fourth lateral surface from the second lateral surface 6122*a*. For example, the second opening OP2 may extend in the first direction D1 between the second lateral surface 6122*a* and an inner surface 6123*a* of the second support stand 6123. The second support member 6122 may include a second support plate 6124 and a second support stand 6123.

The second support plate 6124 may be spaced apart from the tray 613 in the third direction D3. The second support plate 6124 may have a top surface 6124*a* and a bottom surface 6124*b* facing each other. The bottom surface 6124*b* of the second support plate 6124 may face the tray 613. The second support plate 6124 may connect the second adsorption pad 6121 and the second support stand 6123 that are spaced apart from each other. The second support plate 6124 may have a rectangular shape when viewed in plan view. However, exemplary embodiments of the inventive concept are not limited thereto.

The second support stand 6123 may be located between and connect the second support plate 6124 and the tray 613. The second support stand 6123 may be disposed beneath the bottom surface 6124*b* of the second support plate 6124. The second support stand 6123 may lie on the top surface of the tray 613. The second support stand 6123 may be positioned below the second adsorption pad 6121.

The second support stand 6123 and the second adsorption pad 6121 may be spaced apart from each other in the first direction D1, as shown in FIGS. 7 and 8. The second support stand 6123 may be adjacent to a first end of the second support plate 6124. The second support stand 6123 may include an inner surface 6123*a* facing the first grip member 611 and an outer surface 6123*b* opposite to the inner surface 6123*a*. The second support stand 6123 may be disposed substantially perpendicular to the second support plate 6124.

The second lateral surface 6122*a* may include a second end of the second support plate 6124. The fourth lateral surface may include the first end of the second support plate 6124 and the outer surface 6123*b* of the second support stand 6123.

The first and second support members 6112 and 6122 may include a material having excellent strength. For example, the first and second support members 6112 and 6122 may include aluminum (Al).

The second adsorption pad 6121 may adsorb the substrate. The second adsorption pad 6121 may be identically configured to the first adsorption pad 6111. The second adsorption pad 6121 may be disposed on the top surface 6124*a* of the second support plate 6124. The second adsorption pad 6121 and the second support stand 6123 may be spaced apart from each other in the first direction D1.

The second opening OP2 may be defined by the second support plate 6124 and the second support stand 6123. The second opening OP2 may be disposed beneath the bottom surface 6124*b* of the second support plate 6124. In an exemplary embodiment, the second opening OP2 may be disposed between the second support plate 6124 and the tray 613. The second opening OP2 may be located between the second adsorption pad 6121 and the tray 613. The second opening OP2 may have a height H2 greater than the height H1 of the second illumination member 320. The height H2 of the second opening OP2 may indicate a spacing distance between the tray 613 and the bottom surface 6124*b* of the second support plate 6124. The second opening OP2 may include a second overlapping area OA2 and a second non-overlapping area NOA2.

The second opening OP2 may have a portion that overlaps the second adsorption pad 6121 and corresponds to the second overlapping area OA2. The second opening OP2 may also have another portion that does not overlap the second adsorption pad 6121 and that corresponds to the second non-overlapping area NOA2. The second non-overlapping area NOA2 may be positioned between the second overlapping area OA2 and the inner surface 6123*a* of the second support stand 6123.

Figure 9:
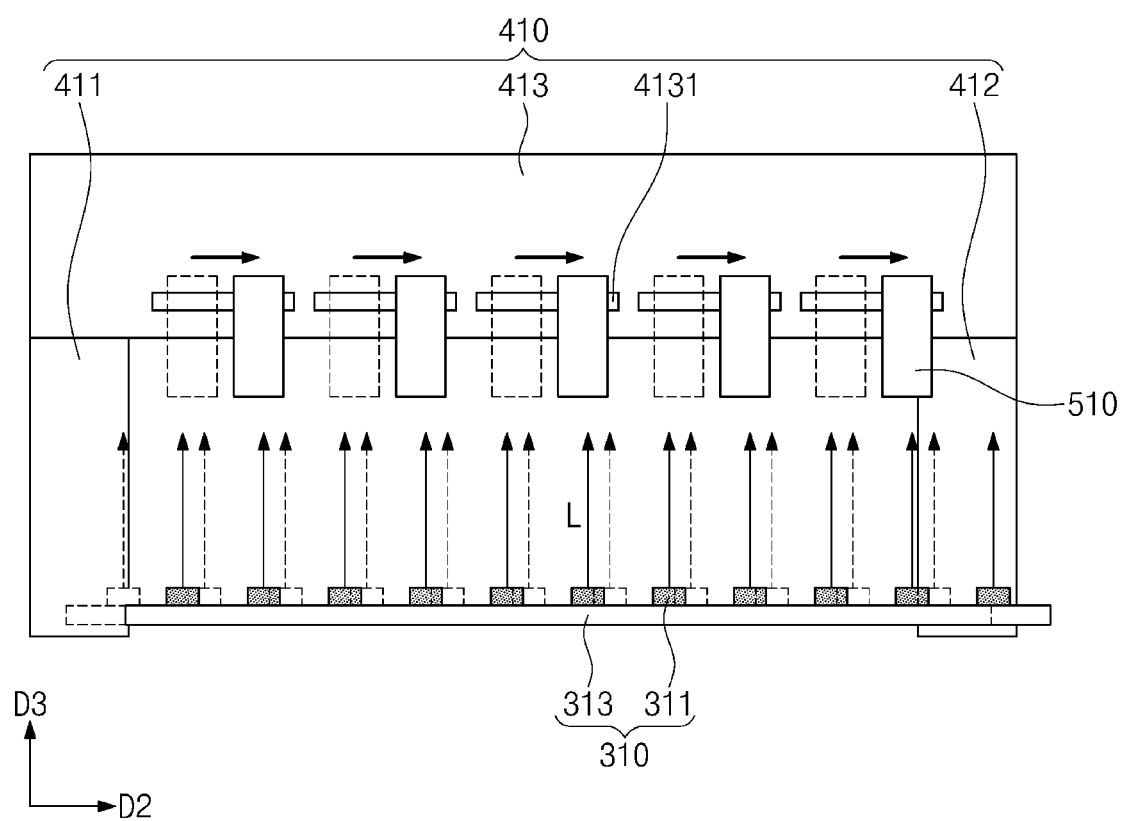
FIG. 9 illustrates a front view showing a first gantry, first optical members, and a first illumination member of FIG. 1 according to an exemplary embodiment of the inventive concept.

FIG. 9 illustrates a front view showing the first gantry, the first optical members, and the first illumination member of FIG. 1, according to an exemplary embodiment of the inventive concept.

Referring to FIGS. 1, 5, and 9, the first gantry 410 may include a first pillar member 411, a second pillar member 412, and a connection member 413. As described above, the second gantry 420 may have the same structure as that of the first gantry 410.

The first and second pillar members 411 and 412 may be spaced apart from each other. For example, the second pillar member 412 may be spaced apart from the first pillar member 411 in the second direction D2.

The connection member 413 may connect the first and second pillar members 411 and 412 to each other. The connection member 413 may be spaced apart from the base 100 in the third direction D3. Thus, a space may be disposed between the connection member 413 and the base 100. The space may accommodate a portion of the floating unit 200 and a portion of the grip unit 610.

The connection member 413 may include a plurality of first guides 4131 that are arranged at a regular distance along the second direction D2. For example, in an exemplary embodiment, the distance between adjacent first guides 4131 arranged in the second direction D2 is about equal for all of the first guides 4131. In an exemplary embodiment, the first guide 4131 may be provided in the form of a groove extending along the second direction D2. In an exemplary embodiment, the first guide 4131 may be provided in the form of a rail extending along the second direction D2.

The first optical members 510 may be engaged with the first gantry 410. For example, the first optical members 510 may be movably installed on the connection member 413. Each of the first optical members 510 may include a second guide that moves along the first guide 4131. In an exemplary embodiment, the second guide may be or may include a guide protrusion inserted into the first guide 4131. As described above, the optical-member moving part may drive the first optical members 510 to reciprocally move along the first guides 4131.

The first illumination member 310 may include a plurality of light sources 311 and a support board 313. The light sources 311 may be disposed on the support board 313. The light sources 311 may be arranged along the second direction D2. The light sources 311 may generate the light L in the third direction D3. In an exemplary embodiment, the light sources 311 may be or may include light emitting diodes (LEDs). However, exemplary embodiments of the inventive concept are not limited thereto. The second illumination member 320 may have the same structure as that of the first illumination member 310.

The support board 313 may have a bar shape elongated in the second direction D2. The illumination moving unit 350 may drive the support board 313. The support board 313 may move in the second direction D2 and in a reverse direction opposite to the second direction D2. In such a configuration, the light sources 311 may move at the same time.

The first illumination member 310 may move in the second direction D2 and in a reverse direction opposite to the second direction D2 in synchronization with movement of the first optical members 510. For example, when the first optical members 510 move in the second direction D2, the first illumination member 310 moves in the second direction D2 at approximately the same time. The first optical members 510 and the first illumination member 310 may be substantially the same in terms of moving distance, moving speed, etc. Accordingly, the light L generated by the first illumination member 310 may be uniformly irradiated onto the first optical members 510. Thus, exemplary embodiments of the inventive concept may enhance uniformity of the light L irradiated onto the first optical members 510, thus, improving substrate inspection performance of the substrate inspection system 10.

Figure 10:
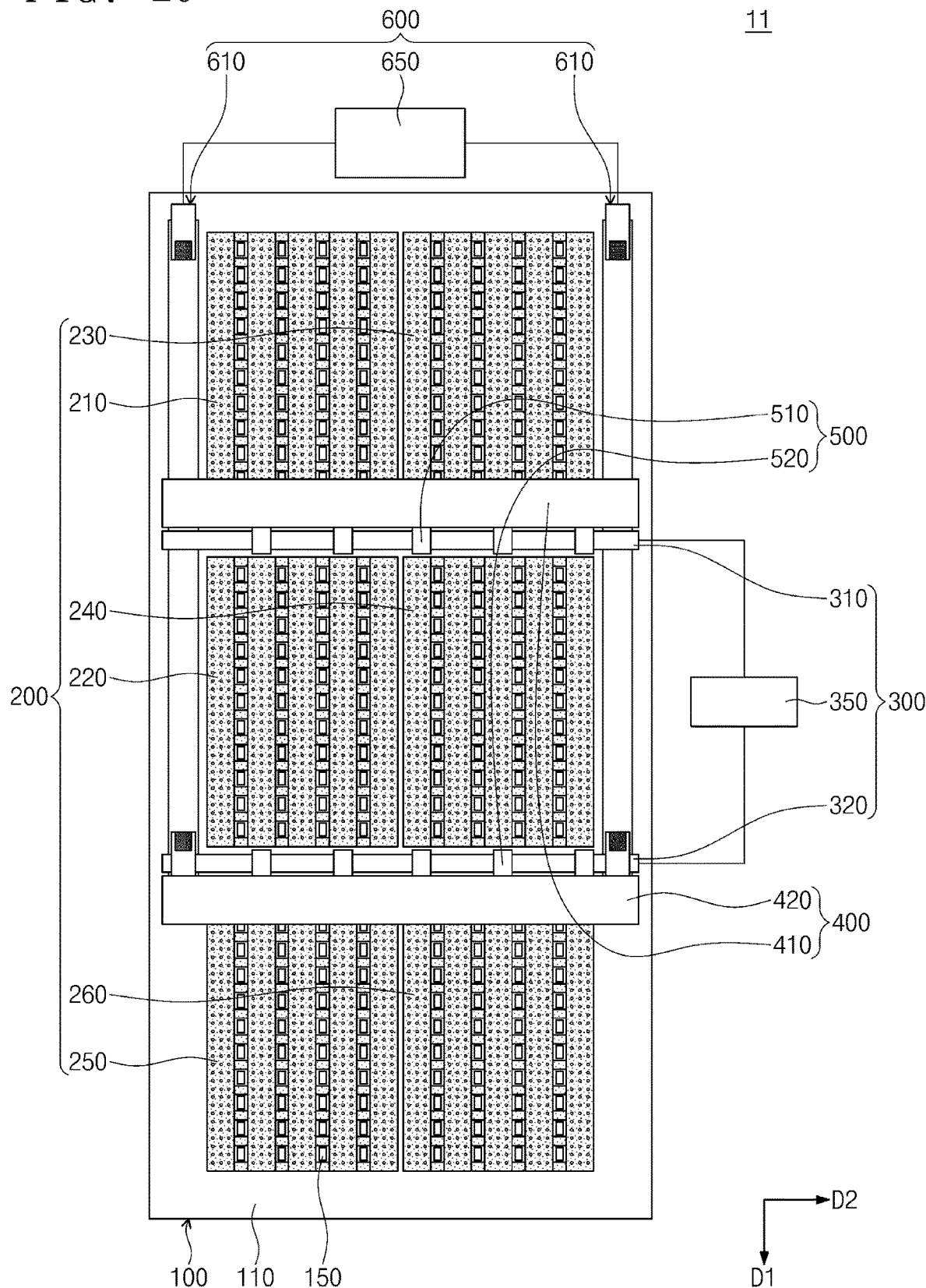
FIG. 10 illustrates a plan view showing a substrate inspection system according to an exemplary embodiment of the inventive concept.

FIG. 10 illustrates a plan view showing a substrate inspection system according to an exemplary embodiment of the inventive concept. For convenience of explanation, a further description of components substantially the same as those previously described with reference to FIGS. 1 to 7 may be omitted.

Referring to FIG. 10, a substrate inspection system 11 according to an exemplary embodiment of the inventive concept may include the base 100, the gantry 400, the floating unit 200, the first substrate transfer unit 150, the inspection unit 500, the illumination unit 300, the illumination moving unit 350, the second transfer unit 600, and the controller (see 700 of FIG. 5).

The second substrate transfer unit 600 may include a plurality of the grip units 610. In an exemplary embodiment, the grip units 610 may include a pair of grip units spaced apart from each other across the floating unit 200. For example, the grip units 610 may include a first grip unit on a side of the floating unit 200 and a second grip unit spaced apart from the first grip unit in the second direction D2. Thus, in an exemplary embodiment, there is no movement area (see MA of FIG. 2) running across the floating unit 200 along the first direction D1. The grip units 610 may have the same structure as each other.

The grip transfer unit 650 may drive the grip units 610 to move in the same direction at approximately the same time.

Figure 11:
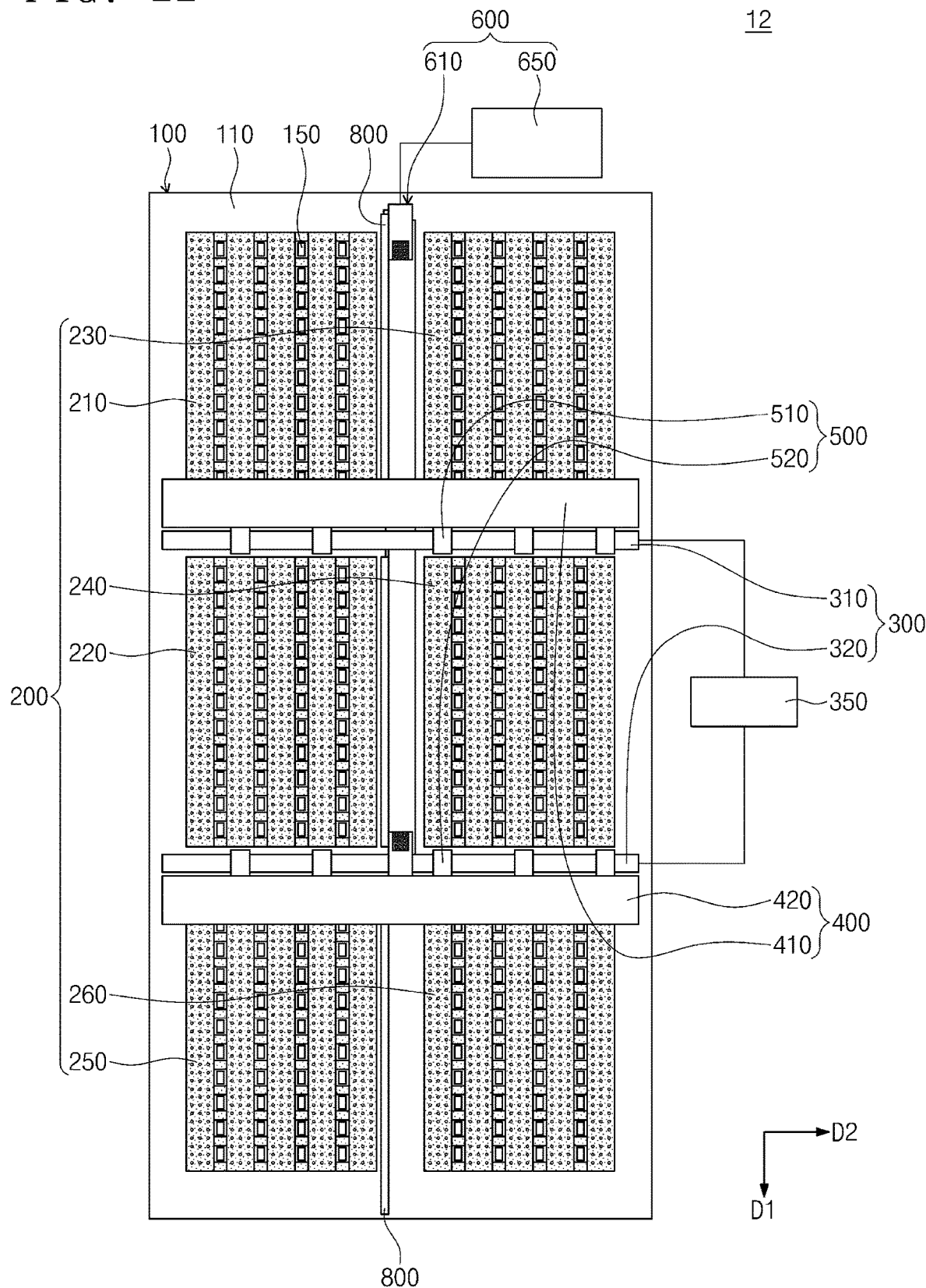
FIG. 11 illustrates a plan view showing a substrate inspection system according to an exemplary embodiment of the inventive concept.
Figure 12:
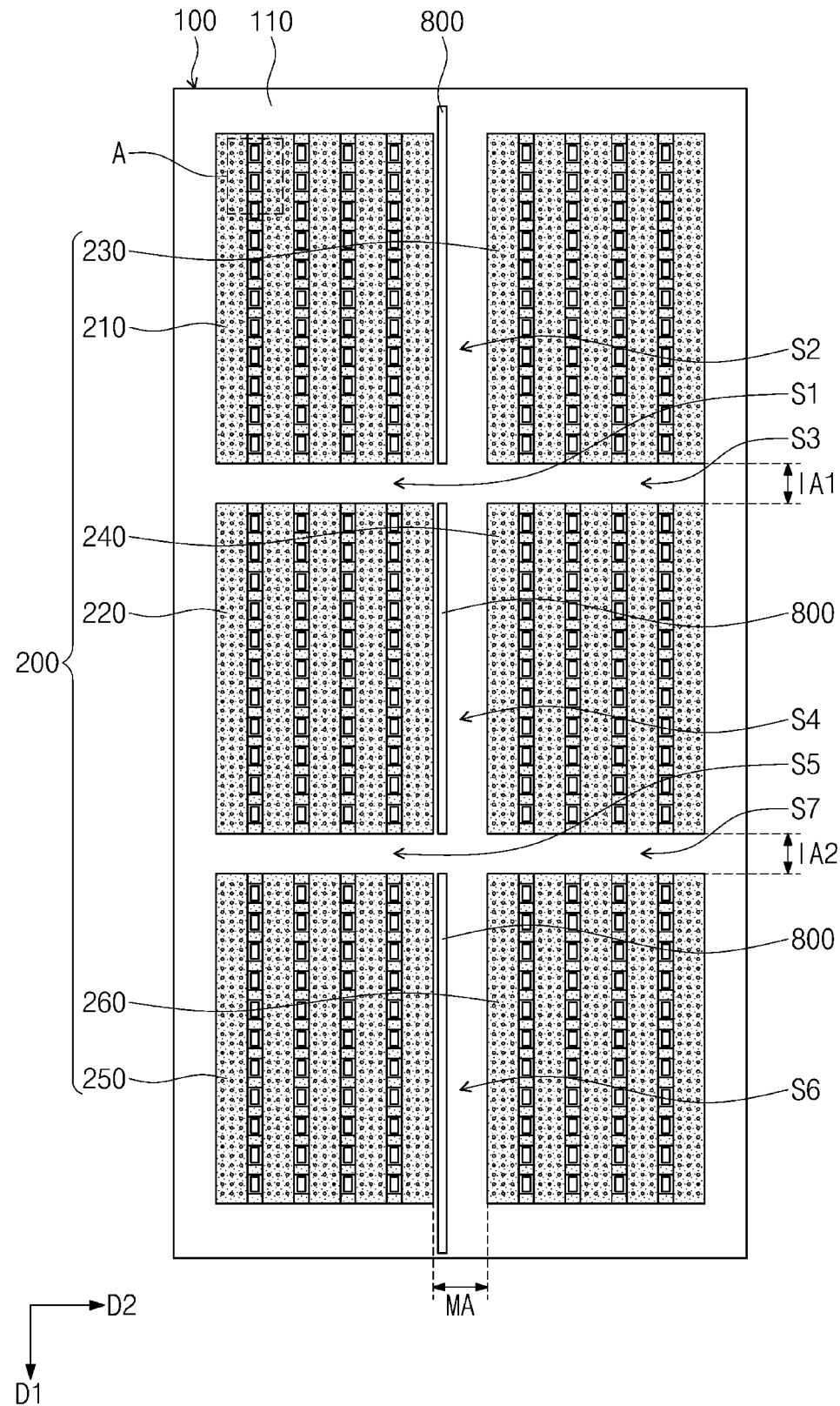
FIG. 12 illustrates a plan view partially showing the substrate inspection system of FIG. 11 according to an exemplary embodiment of the inventive concept.

FIG. 11 illustrates a plan view showing a substrate inspection system according to an exemplary embodiment of the inventive concept. FIG. 12 illustrates a plan view partially showing the substrate inspection system of FIG. 11 according to an exemplary embodiment of the inventive concept. For convenience of explanation, a further description of components substantially the same as those previously described with reference to FIGS. 1 to 7 may be omitted.

Referring to FIGS. 11 and 12, a substrate inspection system 12 according to an exemplary embodiment of the inventive concept may include the base 100, the gantry 400, the floating unit 200, the first substrate transfer unit 150, the inspection unit 500, the illumination unit 300, the illumination moving unit 350, the second transfer unit 600, and the controller (see 700 of FIG. 5). The substrate inspection system 12 may further include a plurality of guide members 800.

The guide members 800 may guide movement of the grip unit 610, while supporting the grip unit 610. The guide members 800 may be disposed on the base 100. The guide members 800 may be disposed within the movement area MA. The guide members 800 may be arranged along the first direction D1. The guide members 800 adjacent to each other may be spaced apart from each other across either the first illumination member 310 or the second illumination member 320. Therefore, interference may be prevented between the guide members 800 and the illumination unit 300.

Figure 13:
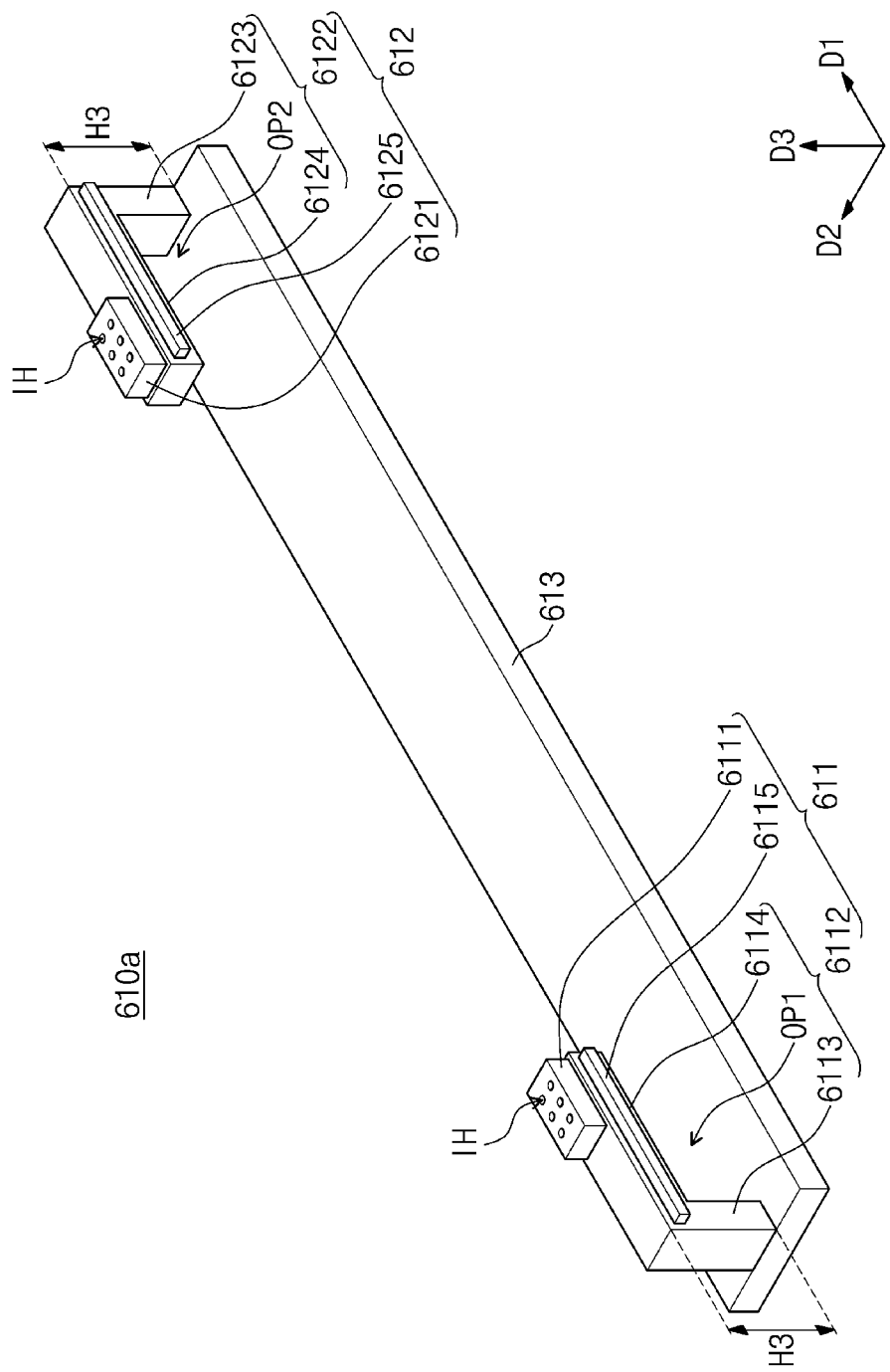
FIG. 13 illustrates a perspective view showing the grip unit of FIG. 11 according to an exemplary embodiment of the inventive concept.

FIG. 13 illustrates a perspective view showing the grip unit of FIG. 11 according to an exemplary embodiment of the inventive concept. For convenience of explanation, a further description of components substantially the same as those previously described with reference to FIGS. 7 and 8 may be omitted.

Referring to FIG. 13, a grip unit 610a may include the first grip member 611, the second grip member 612, and the tray 613.

The first grip member 611 may include the first adsorption pad 6111 and the first support member 6112, and further include a first guide bar 6115. The first support member 6112 may include the first support stand 6113, the first support plate 6114, and the first opening OP1.

The first guide bar 6115 may be disposed on the first support plate 6114. The first guide bar 6115 may be positioned between the first adsorption pad 6111 and the first opening OP1. In an exemplary embodiment, the first guide bar 6115 may be elongated along the first direction D1.

The second grip member 612 may include the second adsorption pad 6121 and the second support member 6122, and further include a second guide bar 6125. The second support member 6122 may include the second support plate 6124 and the second support stand 6123.

The second guide bar 6125 may be disposed on the second support plate 6124. The second guide bar 6125 may be positioned between the second adsorption pad 6121 and the second opening OP2. In an exemplary embodiment, the second guide bar 6125 may be elongated along the first direction D1.

Figure 14:
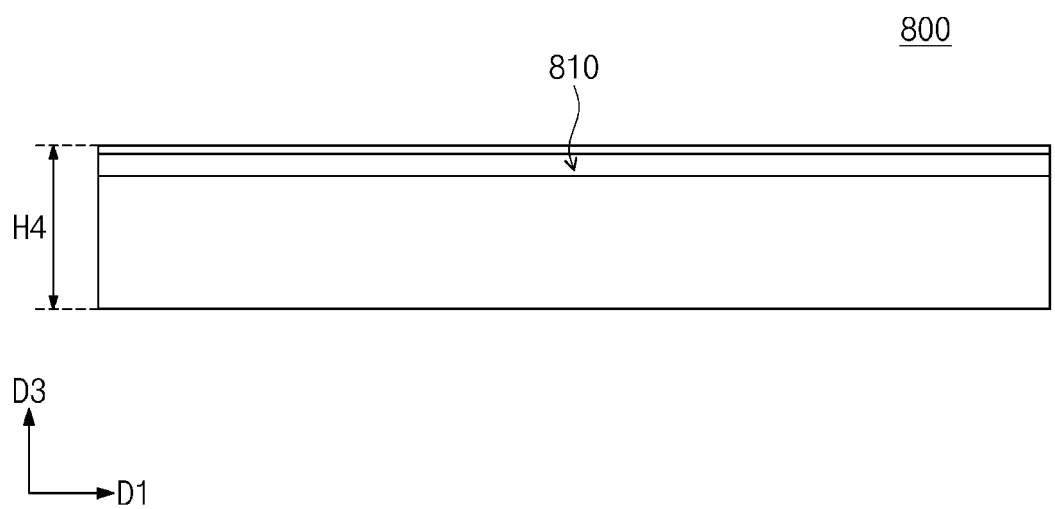
FIG. 14 illustrates a side view showing the guide member of FIG. 11 according to an exemplary embodiment of the inventive concept.

FIG. 14 illustrates a side view showing the guide member of FIG. 11 according to an exemplary embodiment of the inventive concept.

Referring to FIGS. 13 and 14, the guide member 800 may include a guide groove 810 into which the first and second guide bars 6115 and 6125 are inserted. The guide groove 810 may be elongated along the first direction D1. The first and second guide bars 6115 and 6125 may move while being inserted into the guide groove 810. Accordingly, the guide member 800 may guide movement of the grip unit 610a.

When the grip transfer unit (see 650 of FIG. 11) accelerates or decelerates movement of the grip unit 610a, a first force in the third direction D3 and a second force in a reverse direction opposite to the third direction D3 may act on the second end of the first support plate 6114 and/or the second end of the second support plate 6124. In a comparative example, the second ends of the first and second support plates 6114 and 6124 may be displaced due to the first force and/or the second force.

As described above, according to exemplary embodiments of the inventive concept, when the grip unit 610a moves while the first and second guide bars 6115 and 6125 are inserted into the guide groove 810, the guide members 800 support the first and second support plates 6114 and 6124. Accordingly, the second ends of the first and second support plates 6114 and 6124 may be prevented from being displaced by the first force and/or the second force.

The guide member 800 may have a height H4 less than a height H3 of each of the first and second support members 6112 and 6122. The guide member 800 may thus not interfere when the grip unit 610a holds the substrate. The height H3 of the first support member 6112 may indicate a spacing distance between the tray 613 and the top surface 6114a of the first support plate 6114. The height H3 of the second support member 6122 may indicate a spacing distance between the tray 613 and the top surface 6124a of the second support plate 6124.

Figure 15:
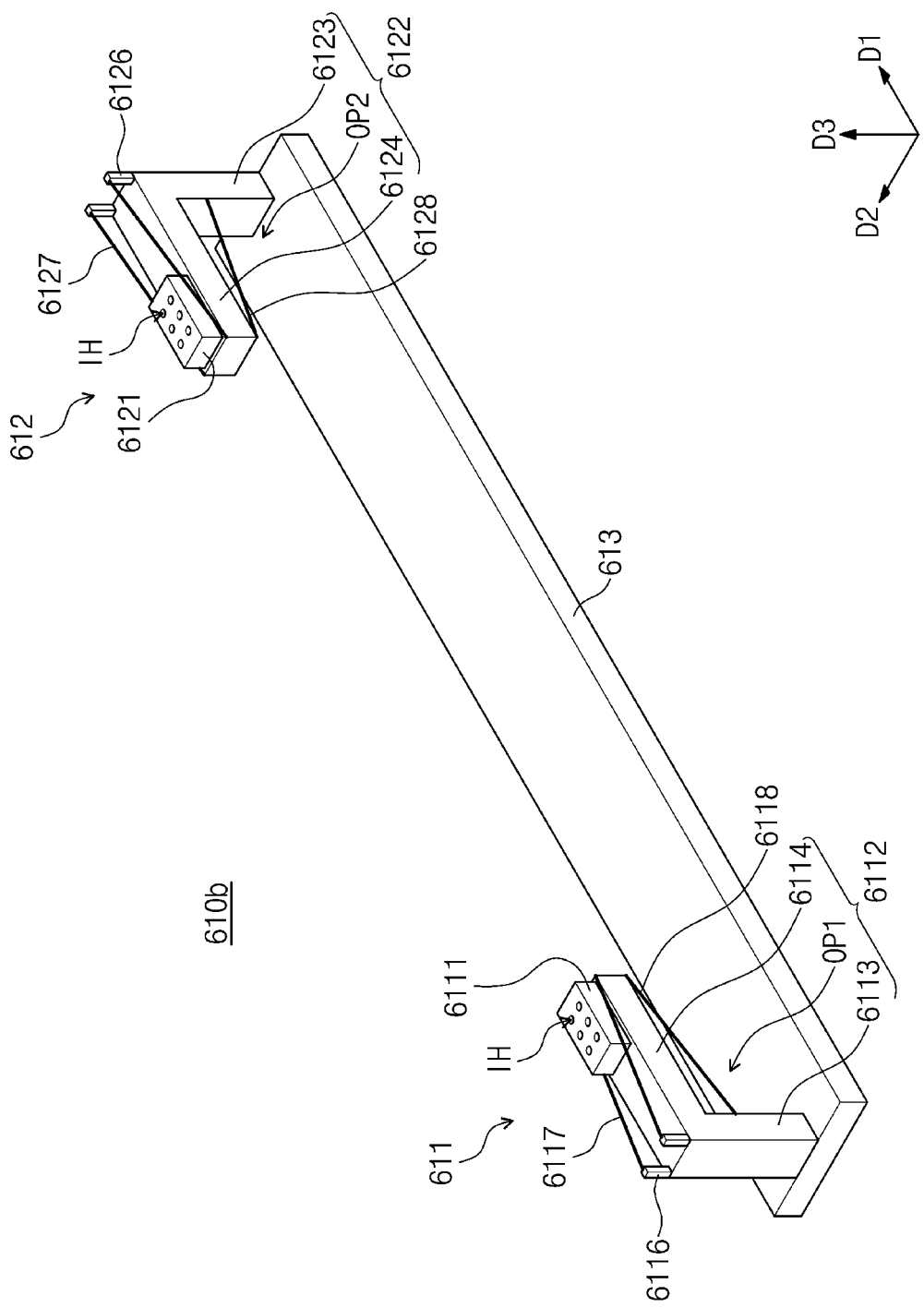
FIG. 15 illustrates a perspective view showing the grip unit of FIG. 1 according to an exemplary embodiment of the inventive concept.
Figure 16:
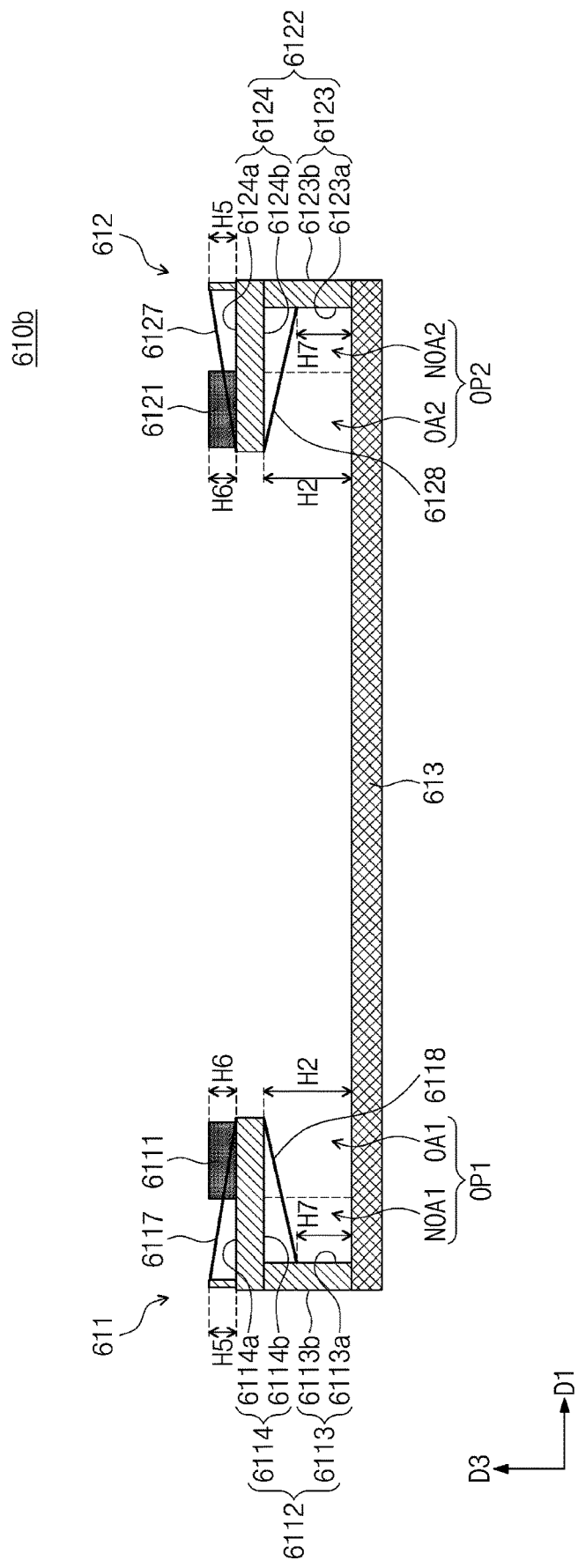
FIG. 16 illustrates a cross-sectional view showing the grip unit of FIG. 15 according to an exemplary embodiment of the inventive concept.

FIG. 15 illustrates a perspective view showing the grip unit of FIG. 1 according to an exemplary embodiment of the inventive concept. FIG. 16 illustrates a cross-sectional view showing the grip unit of FIG. 15 according to an exemplary embodiment of the inventive concept. For convenience of explanation, a further description of components substantially the same as those previously described with reference to FIGS. 7 and 8 may be omitted.

Referring to FIGS. 15 and 16, a grip unit 610b may include the first grip member 611, the second grip member 612, and the tray 613.

The first grip member 611 may include the first adsorption pad 6111 and the first support member 6112, and further include a first protrusion 6116, a first upper wire 6117, and a first lower wire 6118. The first support member 6112 may include the first support plate 6114 and the first support stand 6113.

The first protrusion 6116 may protrude in the third direction D3 from the top surface 6114a of the first support plate 6114. The first protrusion 6116 may have a pillar shape. However, exemplary embodiments of the inventive concept are not limited thereto. The first protrusion 6116 may be adjacent to the first end of the first support plate 6114. The first protrusion 6116 may overlap (e.g., vertically overlap) the first support stand 6113.

The first protrusion 6116 may have a height H5 corresponding to a height H6 of the first adsorption pad 6111.

Accordingly, the first protrusion 6116 may not interfere when the substrate is held on the first adsorption pad 6111. The first protrusion 6116 may be provided in plural. In an exemplary embodiment, a pair of first protrusions 6116 may be provided. The pair of first protrusions 6116 may be arranged along the second direction D2.

The first upper wire 6117 may connect the first protrusion 6116 to the top surface 6114a of the first support plate 6114. For example, a first end of the first upper wire 6117 may be connected to the first protrusion 6116, and a second end of the first upper wire 6117 may be connected to the top surface 6114a of the first support plate 6114. In an exemplary embodiment, the second end of the first upper wire 6117 may be adjacent to the second end of the first support plate 6114, and the first end of the first upper wire 6117 may be adjacent to a top end of the first protrusion 6116. In such a configuration, the first upper wire 6117 may prevent the second end of the first support plate 6114 from being displaced in a reverse direction opposite to the third direction D3.

The first lower wire 6118 may connect the bottom surface 6114b of the first support plate 6114 to the inner surface 6113a of the first support stand 6113. For example, a first end of the first lower wire 6118 may be connected to the inner surface 6113a of the first support stand 6113, and a second end of the first lower wire 6118 may be connected to the bottom surface 6114b of the first support plate 6114. In an exemplary embodiment, the second end of the first lower wire 6118 may be adjacent to the second end of the first support plate 6114. In such a configuration, the first lower wire 6118 may prevent the second end of the first support plate 6114 from being displaced in the third direction D3.

The first end of the first lower wire 6118 may be disposed higher than the first illumination member (see 310 of FIG. 3). For example, a vertical distance H7 between the tray 613 and the first end of the first lower wire 6118 may be greater than the height (see H1 of FIG. 4) of the first illumination member 310. Accordingly, the first lower wire 6118 may not interfere when the first illumination member 310 is inserted into the first opening OP1.

The second grip member 612 may include the second adsorption pad 6121 and the second support member 6122, and further include a second protrusion 6126, a second upper wire 6127, and a second lower wire 6128. The second support member 6122 may include the second support plate 6124 and the second support stand 6123.

The second protrusion 6126, the second upper wire 6127, and the second lower wire 6128 may be respectively configured substantially the same as the first protrusion 6116, the first upper wire 6117, and the first lower wire 6118. Therefore, a description thereof will be omitted.

The following description describes operation of the substrate inspection apparatus configured as described above according to exemplary embodiments of the inventive concept.

FIGS. 17 to 20 illustrate side views showing the substrate inspection system of FIG. 1 operating in substrate inspection according to an exemplary embodiment of the inventive concept.

Figure 17:
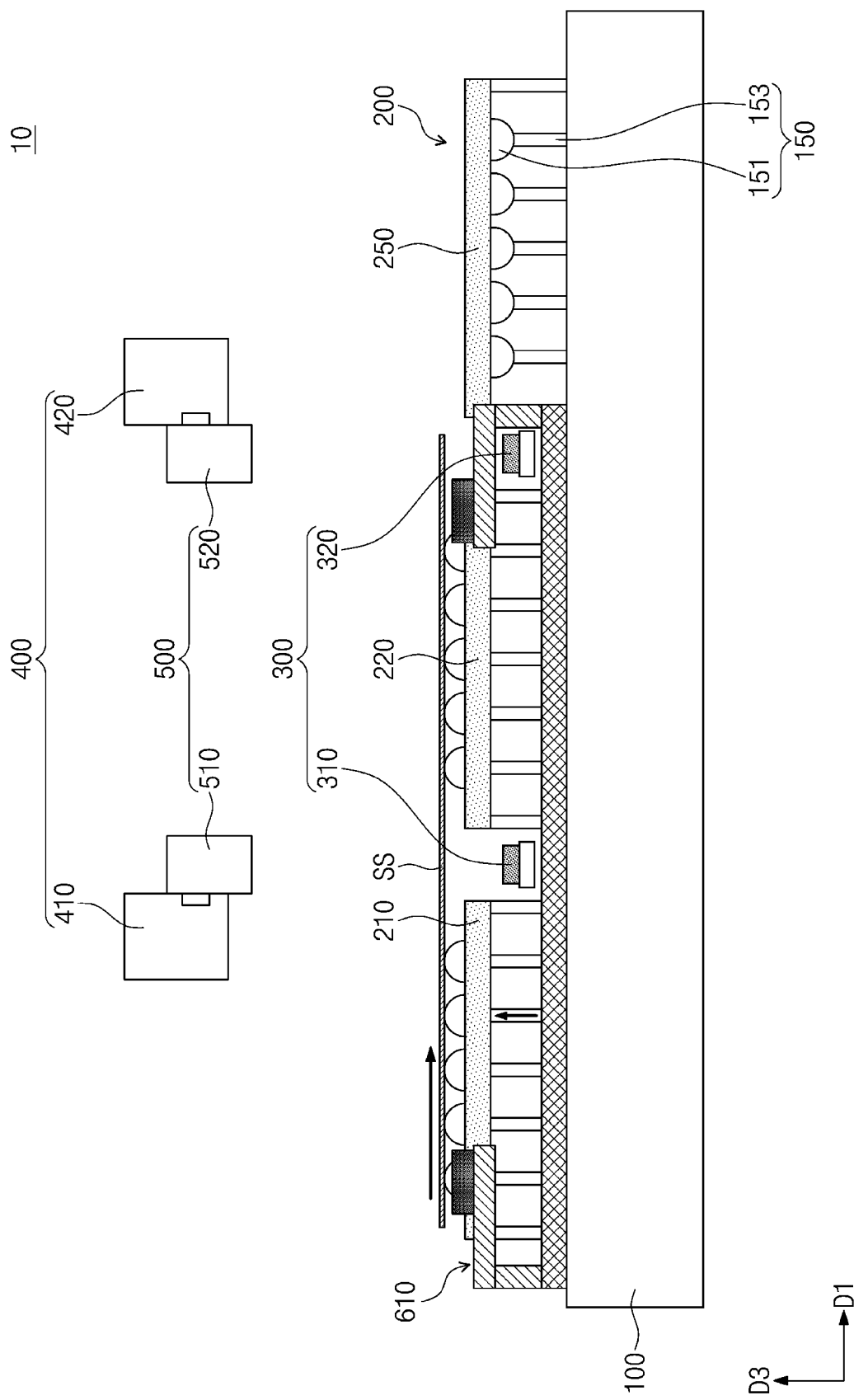
FIGS. 17 to 20 illustrate schematic diagrams showing the substrate inspection system of FIG. 1 operating in substrate inspection according to an exemplary embodiment of the inventive concept.

Referring to FIGS. 1, 6, and 17, the first substrate transfer unit 150 may drive a non-inspected substrate SS to move onto the floating unit 200. For example, the elevating part 153 may raise the rollers 151 in the third direction D3. The rollers 151 may pass through the through holes TH and then protrude beyond the floating stages 210, 220, 230, 240, 250, and 260. The protruded rollers 151 may support the substrate SS. The rotating part may rotate the rollers 151. When the rollers 151 rotate, the substrate SS moves in the first direction D1 on the floating unit 200. In this operation, the substrate SS may be spaced apart from the floating unit 200.

Figure 18:
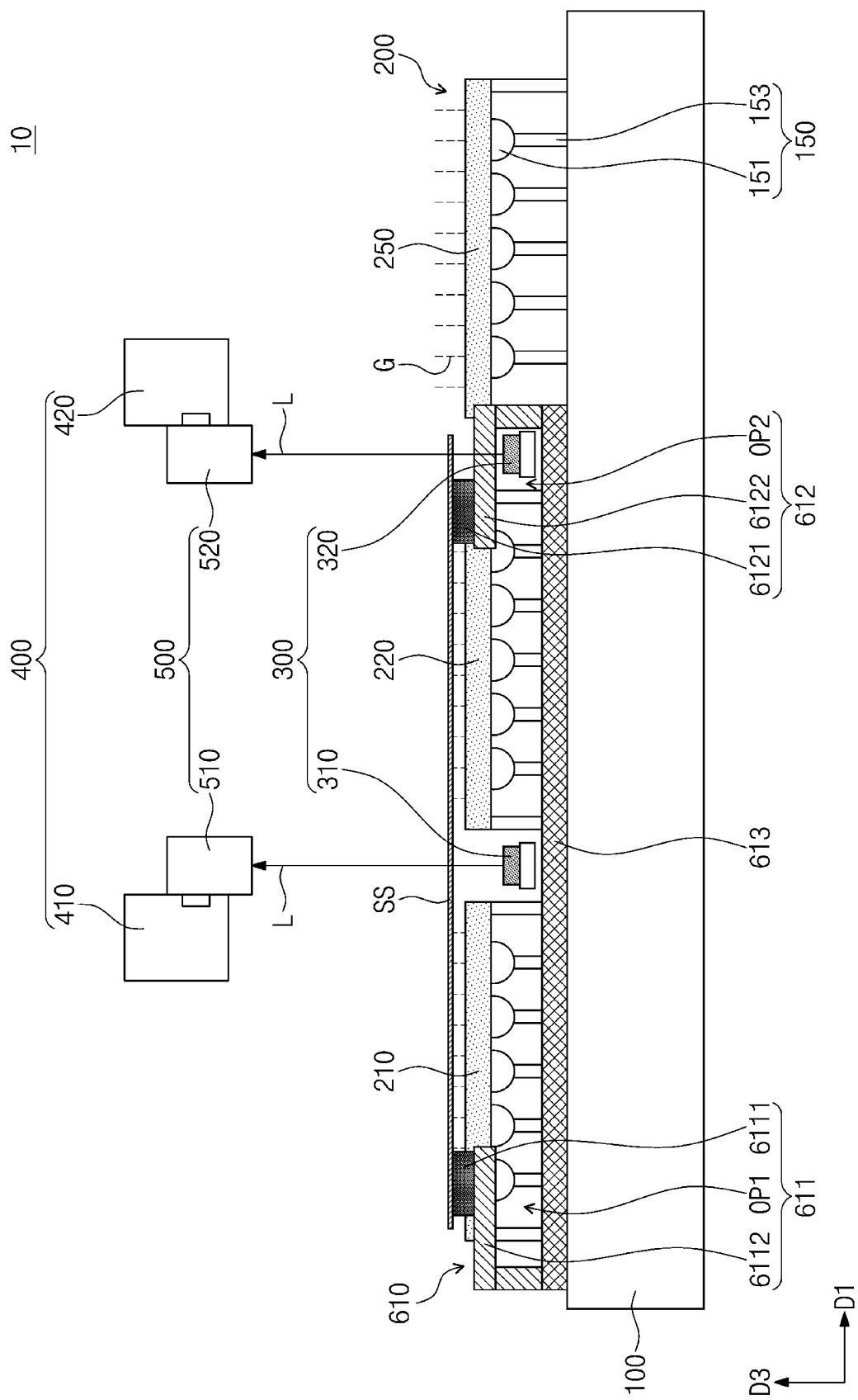

Referring to FIGS. 1 and 18, the elevating part 153 may lower the rollers 151 in a reverse direction opposite to the third direction D3. The floating unit 200 may inject the gas G toward the substrate SS, causing the substrate SS to float on the floating unit 200.

The grip unit 610 may hold the floated substrate SS. For example, the first and second adsorption pads 6111 and 6121 may adsorb the substrate SS.

The illumination unit 300 may generate the light L in a direction toward the inspection unit 500 and/or the substrate SS, irradiating the inspection unit 500 and/or the substrate SS with the light L. As described above, the substrate SS may be transparent to the light L. The optical members 510 and 520 of the inspection unit 500 may receive the light L passing through the substrate SS. The optical members 510 and 520 may use the received light L to obtain the image information (see I of FIG. 5).

For example, the first illumination member 310 may be disposed between the first and second grip members 611 and 612, and may overlap an intermediate region of the substrate SS. The first illumination member 310 may generate the light L in a direction toward the intermediate region of the substrate SS, thus, irradiating the intermediate region of the substrate SS with the light L. The first optical members 510 may receive the light L passing through the intermediate region of the substrate SS.

The second illumination member 320 may be inserted into the second opening OP2. For example, the second illumination member 320 may be disposed within the second non-overlapping area (see NOA2 of FIG. 8). At this moment, the second non-overlapping area NOA2 may overlap an end region of the substrate SS. The second illumination member 320 may then generate the light L in a direction toward the end region of the substrate SS, thus, irradiating the end region of the substrate SS with the light L. The second optical members 520 may receive the light L passing through the end region of the substrate SS. Therefore, the substrate inspection system 10 may inspect the intermediate and end regions of the substrate SS.

Figure 19:
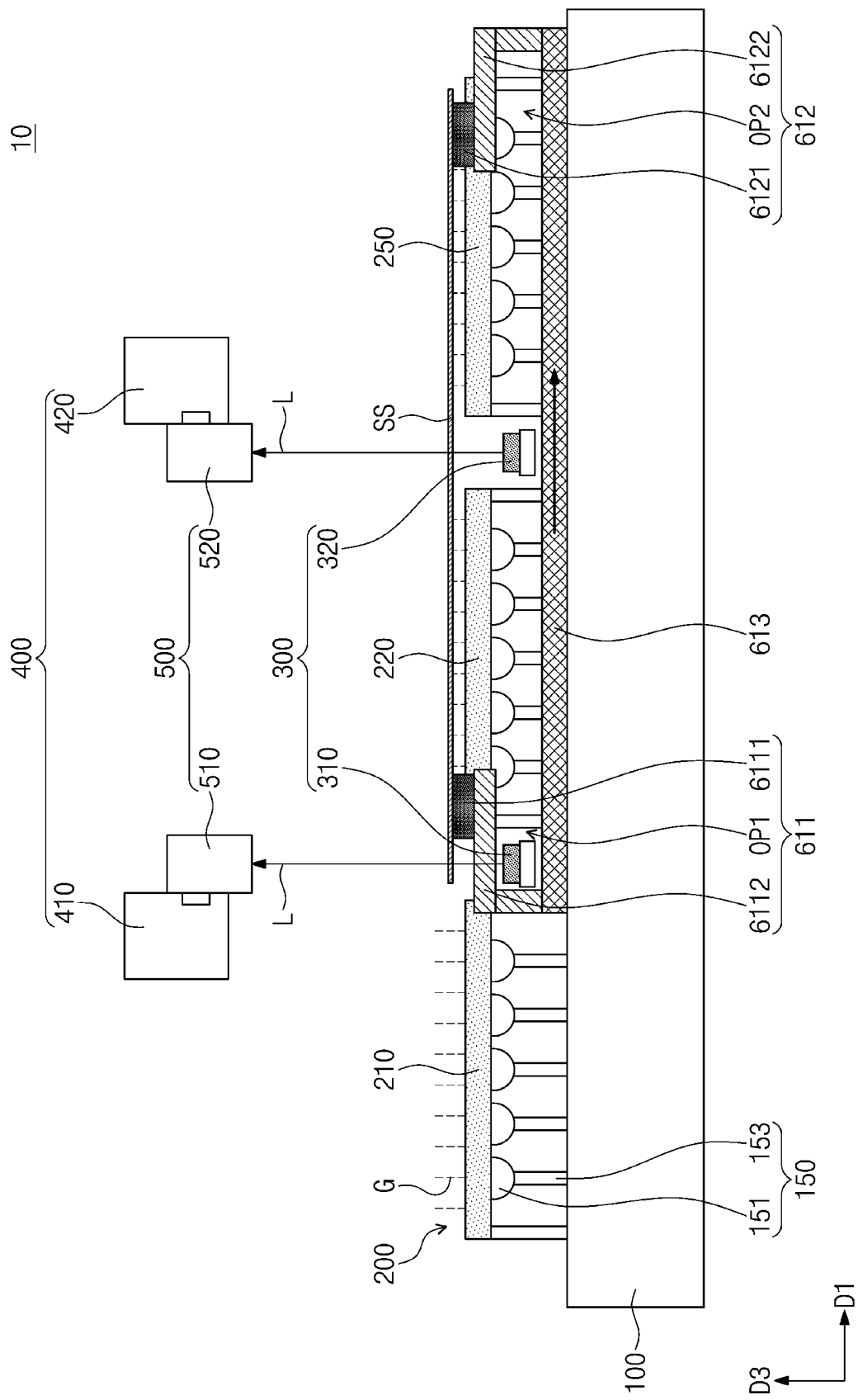

Referring to FIGS. 1 and 19, the grip transfer unit 650 may drive the grip unit 610 to move in the first direction D1. The first illumination member 310 may then be inserted into the first opening OP1. For example, the first illumination member 310 may be disposed within the first non-overlapping area (see NOA1 of FIG. 8). At this moment, the first non-overlapping area NOA2 may overlap an opposite end region of the substrate SS. The first illumination member 310 may then generate the light L in a direction toward the opposite end region of the substrate SS, thus, irradiating the opposite end region of the substrate SS with the light L. In addition, as the grip unit 610 moves in the first direction D1, the first illumination member 310 may also generate the light L in a direction toward a first region between the intermediate and opposite end regions of the substrate SS, thus, irradiating the first region between the intermediate and opposite end regions of the substrate SS with the light L.

As the grip transfer unit 650 drives the grip unit 610 to move in the first direction D1, the second illumination member 320 may also generate the light L in a direction toward a second region between the intermediate and end regions of the substrate SS, thus, irradiating the second region between the intermediate and end regions of the substrate SS with the light L. Therefore, the substrate inspection system 10 may inspect the first region, the second region, the end region, and the opposite end region of the substrate SS. As a result, the substrate inspection system 10 may reduce or minimize a non-inspected region(s) of the substrate SS.

Figure 20:
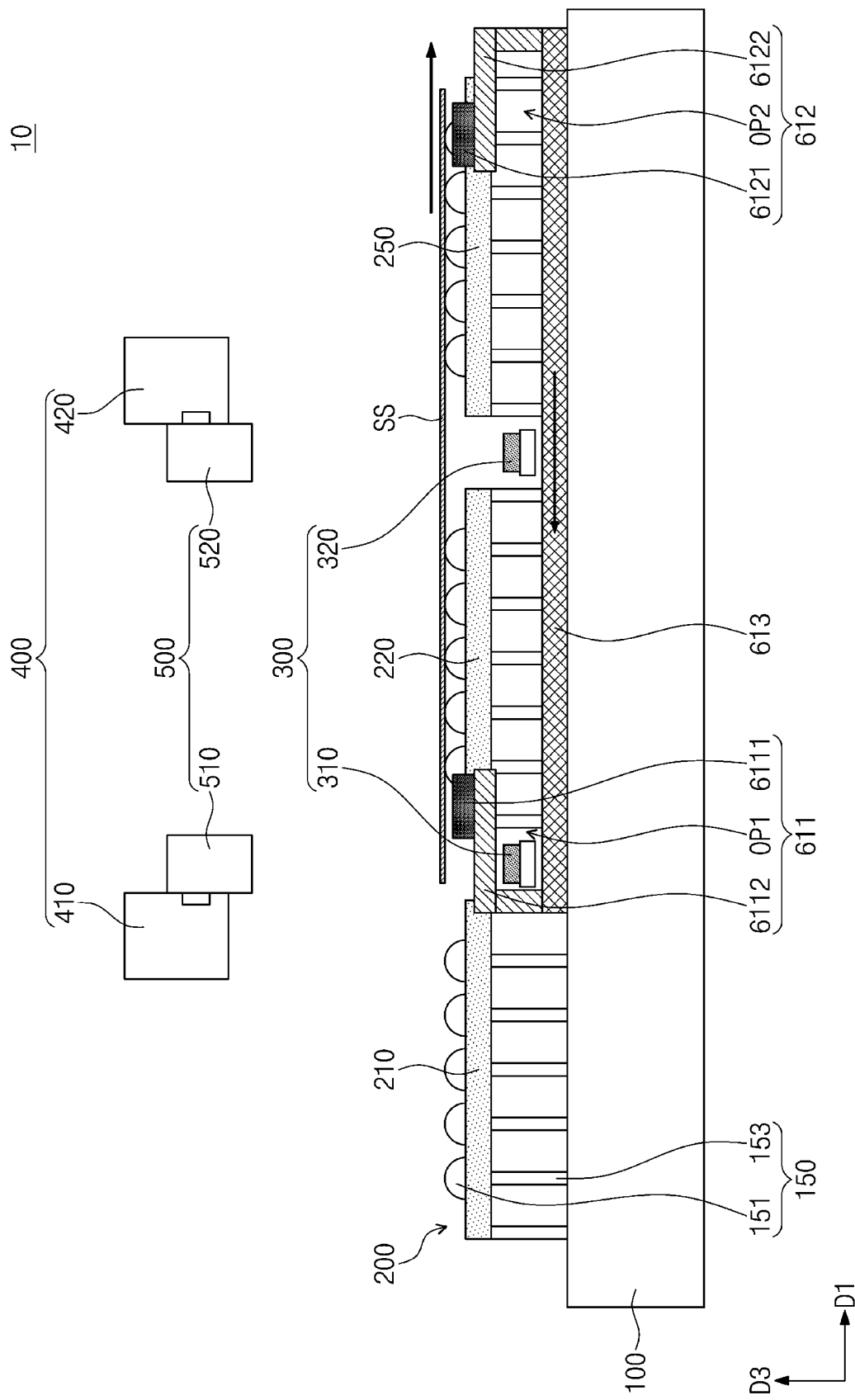

Referring to FIGS. 1 and 20, the elevating part 153 may raise the rollers 151 in the third direction D3. The rollers 151 may thus support the substrate SS again. The rotating part may rotate the rollers 151, and the first substrate transfer unit 150 may move the inspected substrate SS in the first direction D1.

The floating unit 200 may stop injecting the gas G. The grip transfer unit 650 may drive the grip unit 610 to move in a reverse direction opposite to the first direction D1. For example, the grip transfer unit 650 may move the grip unit 610 back to its initial position. After the grip unit 610 moves back to its initial position, the aforementioned steps may be repeatedly performed.

According to exemplary embodiments of the inventive concept, the substrate inspection system described above may be used to perform a method of manufacturing a semiconductor device. The method may include, for example, forming the semiconductor device using the substrate SS, and testing the substrate SS using the substrate inspection system. Testing the substrate SS may include floating the substrate SS using the floating unit 200, holding the substrate SS on the floating unit 200 using the grip unit 610, in which the grip unit 610 includes the first grip member 611 and the second grip member 612 spaced apart from each other, moving the grip unit 610 by the grip transfer unit 650, generating the light L by the illumination member 310/320 disposed between the first and second grip members 611/612, in which the light L is irradiated onto the substrate SS, and inspecting the substrate SS floating on the floating unit 200 by the inspection unit 500, in which the light L is irradiated onto the inspection unit 500 through the substrate SS, and in which the inspection unit 500 inspects the substrate SS using the light L irradiated onto the inspection unit 500.

According to exemplary embodiments of the inventive concept, when the substrate moves while being held in the grip apparatus, interference may be minimized or prevented between the grip apparatus and the illumination unit. Most regions of the substrate may therefore be irradiated with the light generated by the illumination unit, and as a result, a non-inspected region(s) of the substrate may be reduced or minimized.

While the present inventive concept has been particularly shown and described with reference to the exemplary embodiments thereof, it will be understood by one of ordinary skill in the art that various changes in form and detail may be made therein without departing from the spirit and scope of the inventive concept as defined by the following claims.

What is claimed is:
1. A substrate inspection system, comprising:
a plurality of floating stages that floats a substrate;
an optical capture device disposed above the plurality of floating stages, wherein the optical capture device inspects the substrate that floats on the plurality of floating stages;
a grip unit disposed below the optical capture device and comprising a first grip member that holds the substrate on the plurality of floating stages;
a motor that moves the grip unit in a first direction; and a light source that generates light, wherein the light source is disposed on a moving path of the grip unit, and the light generated by the light source is irradiated onto the optical capture device, wherein the first grip member comprises:
a first adsorption pad that adsorbs the substrate; and
a first support member that supports the first adsorption pad and that comprises a first opening into which the light source is inserted.

2. The system of claim 1, wherein the first support member comprises:
a first support plate having a top surface and a bottom surface facing each other; and
a first support stand extending from the bottom surface of the first support plate,
wherein the first adsorption pad is disposed on the top surface of the first support plate and is spaced apart from the first support stand in the first direction,
wherein the first opening is disposed below the bottom surface of the first support plate.

3. The system of claim 2, wherein the first opening comprises:
an overlapping area that overlaps the first adsorption pad; and
a non-overlapping area that does not overlap the first adsorption pad,
wherein the non-overlapping area is disposed between the overlapping area and the first support stand.

4. The system of claim 1, wherein the grip unit further comprises:
a second grip member that holds the substrate and is spaced apart from the first grip member in the first direction,
wherein the second grip member comprises:
a second adsorption pad that adsorbs the substrate; and
a second support member that supports the second adsorption pad and that comprises a second opening into which the light source is inserted.

5. The system of claim 4, Wherein the second support member comprises:
a second support plate having a top surface and a bottom surface facing each other; and
a second support stand extending from the bottom surface of the second support plate and spaced apart from the second adsorption pad in the first direction,
wherein the second adsorption pad is disposed on the top surface of the second support plate,
wherein the second opening is disposed below the bottom surface of the second support plate.

6. The system of claim 5, wherein the second opening comprises:
an overlapping area that overlaps the second adsorption pad; and
a non-overlapping area that does not overlap the second adsorption pad,
wherein the non-overlapping area is disposed between the overlapping area and the second support stand.

7. The system of claim 4, wherein the light source is disposed between the first grip member and the second grip member.

8. The system of claim 4, wherein the grip unit further comprises:
a tray that connects the first grip member to the second grip member,
wherein the first opening is disposed between the first adsorption pad and the tray, and the second opening is disposed between the second adsorption pad and the tray.

9. The system of claim 1, wherein the plurality of floating stages comprises:
a first floating stage that injects a gas toward the substrate; and
a second floating stage that injects the gas toward the substrate, wherein the second floating stage is spaced apart from the first floating stage in the first direction,
wherein the light source comprises a first illumination member disposed between the first and second floating stages and extending in a second direction intersecting the first direction.

10. The system of claim 9, wherein the first illumination member comprises a plurality of light sources arranged in the second direction.

11. The system of claim 9, wherein the plurality of floating stages further comprises:
a third floating stage that injects the gas toward the substrate, wherein the third floating stage is spaced apart from the first floating stage in the second direction; and
a fourth floating stage that injects the gas toward the substrate, wherein the fourth floating stage is spaced apart from the second floating stage in the second direction,
wherein the motor drives the grip unit to move between the first and third floating stages and between the second and fourth floating stages.

12. The system of claim 11, wherein
the fourth floating stage is spaced apart from the third floating stage in the first direction, and
the first illumination member extends between the third and fourth floating stages.

13. The system of claim 9, wherein the light source further comprises:
a second illumination member spaced apart front the first illumination member in the first direction and extending in the second direction.

14. The system of claim 9, wherein the optical capture device comprises:
a plurality of first optical members overlapping the first illumination member and arranged in the second direction.

15. The system of claim 14, wherein
the first optical members move in the second direction, and
the first illumination member moves in the second direction in synchronization with movement of the first optical members.

16. A substrate inspection system, comprising:
a plurality of floating stages that floats a substrate;
a grip unit that holds the substrate on the plurality of floating stages, wherein the grip unit comprises a first grip member and a second grip member spaced apart from each other;
a first illumination member disposed between the first and second grip members, wherein the first illumination member irradiates a light onto the substrate; and
a motor that moves the grip unit,
wherein each of the first and second grip members comprises:
an adsorption pad that adsorbs the substrate;

a support stand disposed below the adsorption pad and spaced apart from the adsorption pad in a direction away from the first illumination member; and a support plate connecting the adsorption pad to the support stand.

17. The system of claim 16, wherein the grip unit further comprises:

a tray connecting the first grip member to the second grip member and spaced apart from the support plate, wherein the support stand connects the tray to the support plate.

18. The system of claim 17, wherein the first illumination member is disposed between the tray and the support plate.

19. The system of claim 16, wherein the plurality of floating stages comprises a first floating stage and a second floating stage spaced apart from each other, and the first illumination member is disposed between the first and second floating stages, wherein the first and second floating stages inject a gas toward the substrate, wherein the first illumination member extends along a space between the first and second floating stages.

20. The system of claim 19, wherein the plurality of floating stages further comprises:

a third floating stage spaced apart from the first floating stage; and a fourth floating stage spaced apart from the second floating stage, wherein the grip unit is disposed between the first and third floating stages, and between the second and fourth floating stages.

* * * * *